United States Patent
Kortz et al.

(10) Patent No.: US 11,452,993 B2
(45) Date of Patent: Sep. 27, 2022

(54) POLYOXOMETALATES COMPRISING NOBLE METALS AND CORRESPONDING METAL CLUSTERS

(71) Applicant: ExxonMobil Chemical Patents Inc., Baytown, TX (US)

(72) Inventors: Ulrich Kortz, Bremen (DE); Yixian Xiang, Bath (GB); Zhengguo Lin, Beijing (CN); Peng Yang, Thuwal (SA); Helge Jaensch, Grimbergen (BE); Wassim W. Ayass, Berlin (DE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 488 days.

(21) Appl. No.: 15/772,586

(22) PCT Filed: Oct. 14, 2016

(86) PCT No.: PCT/EP2016/074665
§ 371 (c)(1),
(2) Date: May 1, 2018

(87) PCT Pub. No.: WO2017/076603
PCT Pub. Date: May 11, 2017

(65) Prior Publication Data
US 2019/0091663 A1    Mar. 28, 2019

(30) Foreign Application Priority Data

Nov. 6, 2015  (EP) ..................................... 15193323
Feb. 4, 2016  (EP) ..................................... 16154308
Jul. 28, 2016  (EP) ..................................... 16181705

(51) Int. Cl.
*B01J 23/66*    (2006.01)
*B01J 21/08*    (2006.01)
(Continued)

(52) U.S. Cl.
CPC ............... *B01J 23/66* (2013.01); *B01J 21/08* (2013.01); *B01J 23/50* (2013.01); *B01J 23/681* (2013.01);
(Continued)

(58) Field of Classification Search
CPC ... B01J 23/66; B01J 21/08; B01J 23/50; B01J 35/026; B01J 37/0215; B01J 37/04; B01J 37/16; B01J 37/348
(Continued)

(56) References Cited

U.S. PATENT DOCUMENTS 4,864,041 A     9/1989  Hill
8,080,493 B2 *  12/2011 Chubarova ............. C07B 41/00
                                                      502/326
(Continued)

FOREIGN PATENT DOCUMENTS

WO    2007/139616 A    12/2007
WO    2007/142727 A1   12/2007
(Continued)

OTHER PUBLICATIONS

Yang, P. et al. "Erdalkalimetalle als Gastionen in der Polyoxopalladatchemie: vom Nanowurfel uber eine offenschalige Strukturzum Nanostern", Angew. Chem.vol. 126, No. 44, pp. 12168-12172, 2014.
(Continued)

*Primary Examiner* — Melissa S Swain

(57) ABSTRACT

The invention relates to polyoxometalates represented by the formula $(A_n)^{m+}\{M'_s[M''M_{12}X_8O_yR_zH_q]\}^{m-}$ or solvates thereof, corresponding supported polyoxometalates, and processes for their preparation, as well as corresponding metal-clusters, optionally in the form of a dispersion in a liquid carrier medium or immobilized on a solid support, and
(Continued)

Figure 1:
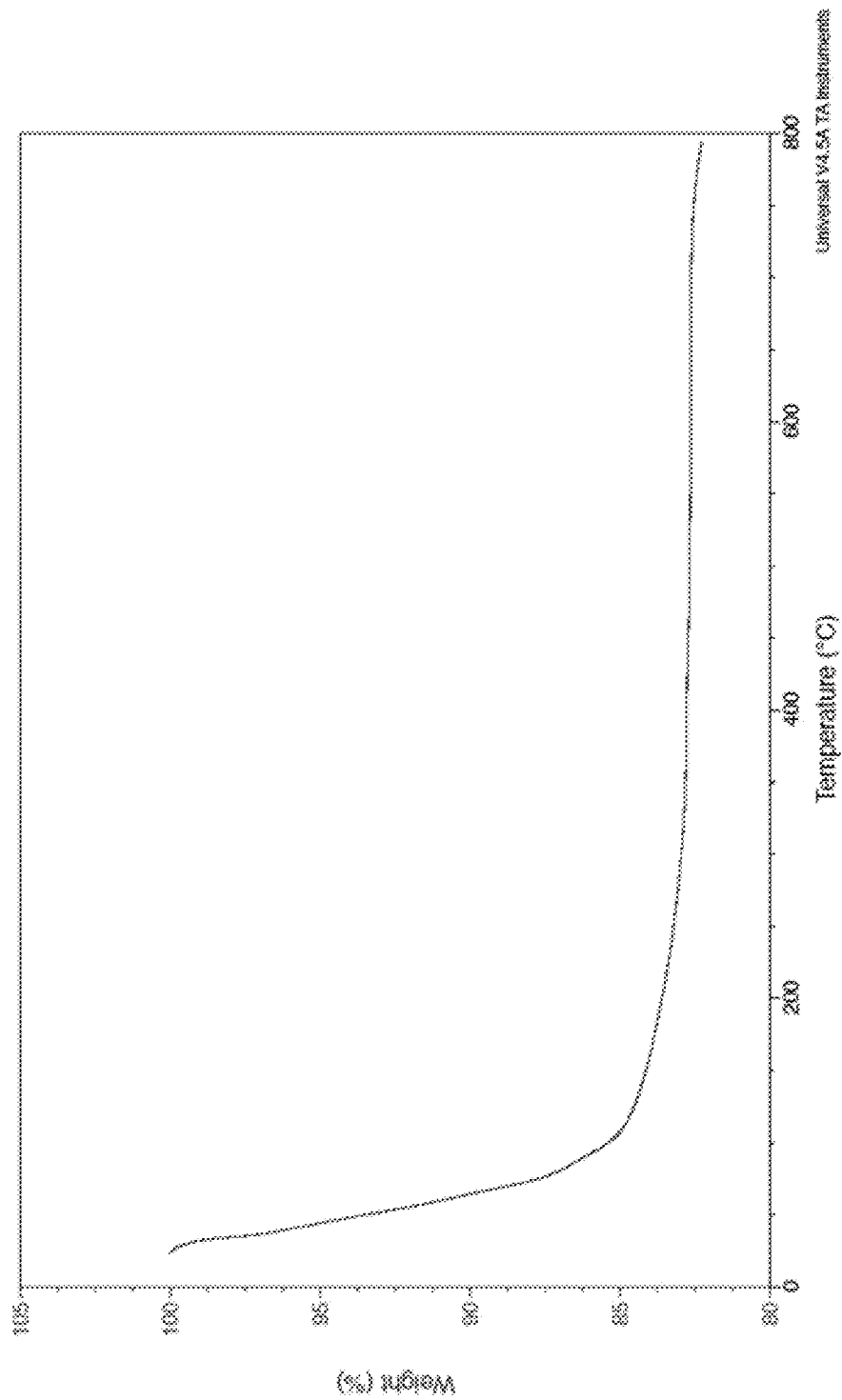

processes for their preparation, as well as their use in reductive conversion of organic substrate.

3 Claims, 6 Drawing Sheets

(51) Int. Cl.
| | |
|---|---|
| *C01G 55/00* | (2006.01) |
| *B01J 23/68* | (2006.01) |
| *B01J 35/00* | (2006.01) |
| *B01J 23/50* | (2006.01) |
| *B01J 35/02* | (2006.01) |
| *B01J 37/02* | (2006.01) |
| *B01J 37/04* | (2006.01) |
| *B01J 37/16* | (2006.01) |
| *B01J 37/34* | (2006.01) |
| *C07C 5/10* | (2006.01) |

(52) U.S. Cl.
CPC .......... *B01J 35/002* (2013.01); *B01J 35/026* (2013.01); *B01J 37/0215* (2013.01); *B01J 37/04* (2013.01); *B01J 37/16* (2013.01); *B01J 37/348* (2013.01); *C01G 55/002* (2013.01); *C07C 5/10* (2013.01); *B01J 2523/00* (2013.01); *C01P 2002/77* (2013.01); *C01P 2002/84* (2013.01); *C01P 2002/88* (2013.01); *C07C 2523/66* (2013.01)

(58) Field of Classification Search
USPC ........................................................ 502/150
See application file for complete search history.

(56) References Cited

U.S. PATENT DOCUMENTS

| | | |
|---|---|---|
| 2005/0112055 A1 | 5/2005 | Shannon et al. |
| 2009/0216052 A1 | 8/2009 | Chubarova et al. |
| 2012/0091448 A1* | 4/2012 | Ueno ................. H01L 51/5088 257/40 |
| 2013/0245337 A1 | 9/2013 | Weiner et al. |

FOREIGN PATENT DOCUMENTS

| | | |
|---|---|---|
| WO | 2007/142729 A | 12/2007 |
| WO | 2008/089065 A | 7/2008 |
| WO | 2008/118619 A | 10/2008 |
| WO | 2009/155185 A | 12/2009 |
| WO | 2010/021600 A | 2/2010 |
| WO | WO-2013128120 A2 * | 9/2013 .......... B01J 23/8896 |
| WO | 2017/076603 A | 5/2017 |
| WO | 2017/133898 A | 8/2017 |

OTHER PUBLICATIONS

Izarova, N. et al. "Self-assembly of star-shaped heteropoly-15-palladate(II)", Dalton Transactions:The International Journal for Inorganic, Organometallic and Bioinorganic Chemistry, No. 43, pp. 9385, 2009.

Xu, F. et al. "A Supramolecular Heteropolyoxopalladate {Pd 15} Cluster Host Encapsulating a {Pd 2} Dinuclear Guest: [Pd II 2 [subset] {H 7 Pd II 15 O 10 (PO 4) 10}] 9-", Journal of the American Chemical Society, vol. 133, No. 13, pp. 4684-4686, 2011.

Izarova, N. et al. "Edelmetalle in Polyoxometallaten", Angew. Chem., vol. 124, No. 38, pp. 9630-9649, 2012.

PCT/EP2017/051101, International Search Report and Written Opinion, dated Mar. 16, 2017.

Negishi, Y. et al. "Magic-Numbered Au n Clusters Protected by Glutathione Monolayers (n = 18, 21, 25, 28, 32, 39): Isolation and Spectroscopic Characterization", Journal of the American Chemical Society, vol. 126, No. 21, pp. 6518-6519, 2004.

Buck, R.P. et al. "Measurement of pH. Definition, Standards, and Procedures" (IUPAC Recommendations 2002), Pure Appl. Chem., vol. 74, No. 11, pp. 2169-2200, 2002.

Brown, I.D., et al. "Bond-Valence Parameters Obtained from a Systematic Analysis of the Inorganic Crystal Structure Detabase", Acta Crystallogr., vol. B41, pp. 244-247, 1985.

Kortz, U. et al. "Self-Assembly of a Heteropolyoxopalladate Nanocube: [PdII 13As v 8 O 34(OH)6]8", Angew. Chem. Int. Ed., vol. 47, pp. 9542-9546, 2008.

Kortz, U. et al. "Noble Metals in Polyoxometalates", Angew. Chem. Int. Ed., vol. 51, pp. 9492-9510, 2012.

Kortz, U. et al. "3d Metal Ions in Highly Unusual Eight-Coordination: The Phosphate-Capped Dodecapalladate (II) Nanocube", Chemistry A European Journal vol. 18, pp. 6167-6171, 2012.

Kortz, U. et al. "The Mixed Gold-Palladium Polyoxo-Noble-Metalate [NaAuIII 4PdII 8 O 8 (AsO4) 8]11", Chemistry A European Journal vol. 20, pp. 8556-8560, 2014.

Cronin, L. et al. "Self-assembly and structural transformations of high-nuclearity palladium-rich polyoxometalates", Inorganic Chemistry Frontiers., vol. 1, pp. 178-185, 2014.

PCT/EP2016/074665, International Search Report and Written Opinion, dated Nov. 15, 2016.

Putaj, P. et al. (2011) "Polyoxometalates Containing Late Transistion and Noble Metal Atoms," *Coordin. Chem. Rev.*, v.255(15-16), pp. 1642-1685.

* cited by examiner

POLYOXOMETALATES COMPRISING NOBLE METALS AND CORRESPONDING METAL CLUSTERS

CROSS REFERENCE TO RELATED APPLICATIONS

This application is a National Phase Application of International Application Serial No. PCT/EP2016/074665, filed 14 Oct. 2016, which claims the benefits of and priorities to European Patent Application Serial No. 15193323.1, filed 6 Nov. 2015, European Patent Application Serial No. 16154308.7, filed 4 Feb. 2016, and European Patent Application Serial No. 16181705.1, filed 28 Jul. 2016, the disclosures of which are fully incorporated by reference in their entireties.

FIELD OF THE INVENTION

This invention relates to new polyoxometalates (POMs) and metal clusters. Furthermore, this invention relates to processes for the preparation of said new POMs and metal-clusters and to their use in catalytic reduction reactions with organic molecules.

BACKGROUND OF THE INVENTION

POMs are a unique class of inorganic metal-oxygen clusters. They consist of a polyhedral cage structure or framework bearing a negative charge which is balanced by cations that are usually external to the cage, and may also contain internally or externally located heteroatom(s) or guest atom(s). The framework of POMs comprises a plurality of metal atoms, which can be the same or different, bonded to oxygen atoms. In the plurality of known POMs the framework metals are dominated by a few elements including transition metals from Group 5 and Group 6 in their high oxidation states, e.g. tungsten (VI), molybdenum (VI), vanadium (V), niobium (V) and tantalum (V).

The first example in the POM family is the so-called Keggin anion $[XM_{12}O_{40}]^{n-}$ with X being a heteroatom selected from a variety of elements, e.g. P, and M being a Group 5 or Group 6 metal such as Mo or W. These anions consist of an assembly of corner- and edge-shared $MO_6$ octahedra of the metals of Groups 5 or 6 around a central $XO_4$ tetrahedron.

There have been increasing efforts towards the modification of polyanions with various organic and/or transition metal complex moieties with the aim of generating new catalyst systems as well as functional materials with interesting optical, electronic, magnetic and medicinal properties. In particular, transition metal-substituted POMs (TMSPs) have attracted continuously growing attention as they can be rationally modified on the molecular level including size, shape, charge density, acidity, redox states, stability, solubility etc. To date many 3d transition metal-containing POMs are known, but still only a minority of POMs contains 4d and 5d metals. However, the introduction of 4d and 5d metals, especially of late 4d and 5d metals, in a POM would be of fundamental interest en route to new, more efficient and more selective catalysts. Especially Rh, Ir, Pd, Pt, Ag and/or Au-containing POMs would be of high interest, because they are thermally and oxidatively stable and possess highly attractive catalytic properties.

For example, Kortz and coworkers reported the first molecular palladium oxide polyanion $[Pd_{13}As_8O_{34}(OH)_6]^{8-}$ in 2008 (Angew. Chem. Int. Ed. 2008, 47, 9542-9546). Twelve palladium atoms surround the thirteenth, the central palladium guest atom, resulting in a distorted icosahedral arrangement. In US 2009/0216052 A1 closely related POMs are disclosed based on this common structural motif comprising $[M_{13}X_8R_qO_y]^{m-}$ with M being selected from Pd, Pt, Au, Rh, Ir, and mixtures thereof, while X is a heteroatom such as As, Sb, Bi, P, Si, Ge, B, Al, Ga, S, Se, Te, and mixtures thereof. These POMs were demonstrated to be useful as catalysts and precursors for mixed metal-oxide catalysts and metal-clusters.

Kortz and coworkers also developed a related class of POMs displaying a similar structural arrangement but a different elemental composition. In the $[MPd_{12}P_8O_{40}H_z]^{m-}$ polyanions the 'inner' '$MO_8$' motif is surrounded by twelve square-planar '$PdO_4$' units and M is represented by Mn, Fe, Co, Cu and Zn (Chem. Eur. J. 2012, 18, 6167-6171).

In 2014 Kortz and coworkers published the first fully inorganic discrete gold-palladium-oxo polyanion $[NaAu_4Pd_8O_8(AsO_4)_8]^{11-}$ without the stabilization of any organic ligands and with both Au and Pd occupying the atom positions of the metal framework. With regard to the structure the cubic '$NaO_8$' moiety is surrounded by 12 noble metal centers forming a cuboctahedron, which is capped by eight tetrahedral arsenate groups (Chem. Eur. J. 2014, 20, 8556-8560).

Cronin and coworkers found three new Pd-containing POMs $K_{28}[H_{12}Pd_{10}Se_{10}W_{52}O_{206}]$, $K_{26}[H_{14}Pd_{10}Se_{10}W_{52}O_{206}]$ and $Na_{40}[Pd_6Te_{19}W_{42}O_{190}]$ demonstrating the structural complexity of some of the late transition metal-containing POMs (Inorg. Chem. Front. 2014, 1, 178-185).

WO 2007/142729 A1 discloses a class of Pd and W as well as Pt and W-based POMs and mixtures thereof with the general formula $[M_y(H_2O)_{(p\cdot y)}X_2W_{22}O_{74}(OH)_2]^{m-}$ with M being Pd, Pt, and mixtures thereof, y being 1 to 4, p being the number of water molecules bound to one M and being 3 to 5 and X being Sb, Bi, As, Se and Te. Protocols for the preparation of these POMs were provided. Furthermore, the POMs were found to be useful as catalysts.

WO 2008/089065 A1 discloses a class of W-based POMs including late transition metals with the formula $[M_y(H_2O)_p X_zW_{18}O_{66}]^{m-}$ with M being Cu, Zn, Pd and Pt and X being selected from the group of halides. The POMs prepared are useful as catalysts.

WO 2007/142727 A1 discloses a class of transition metal-based POMs including W having the formula $[M_4(H_2O)_{10}(XW_9O_{33})_2]^{m-}$ with M being a transition metal and X being selected from As, Sb, Bi, Se and Te. These POMs are particularly useful as catalysts featuring high levels of conversion in selective alkane oxidation.

WO 2008/118619 A1 discloses another class of transition metal-based POMs including W which is illustrated by the general formula $[H_qM_{16}X_8W_{48}O_{184}(HO)_{32}]^{m-}$ with M being selected from the group of transition metals and X being selected from As and/or P. Protocols for the preparation of these POMs were developed. Furthermore, the POMs were found to be useful as catalysts.

US 2005/0112055 A1 discloses a POM including three different transition metals Ru, Zn and W with the formula $Na_{14}[Ru_2Zn_2(H_2O)_2(ZnW_9O_{34})_2]$. This particular POM was found to be highly efficient as an electrocatalyst in the generation of oxygen.

WO 2007/139616 A1 discloses a class of W-based POMs including Ru with the formula $[Ru_2(H_2O)_6X_2W_{20}O_{70}]^{m-}$ with X being selected from Sb, Bi, As, Se, and Te. Protocols for the preparation of these POMs are described. Furthermore, the POMs were found to be useful as catalysts.

WO 2009/155185 A1 discloses a class of Ru and W-based POMs provided by the general formula [Ru$_2$L$_2$(XW$_{11}$O$_{39}$)$_2$WO$_2$]$^{m-}$ with L being a ligand and X being Si, Ge, B and mixtures thereof. The POMs are useful as catalysts and precursors for the preparation of mixed metal-oxide catalysts.

U.S. Pat. No. 4,864,041 in general demonstrates the potential of POMs as catalysts for the oxidation of organic compounds. A variety of different POMs with different metal species was investigated, including those with W, Mo, V, Cu, Mn, Fe, Fe and Co.

WO 2010/021600 A1 discloses a method for preparing POMs and reducing them. Thus, for example metallic nanoparticles can be derived. Specifically W-based POMs are discussed.

Two reviews on POM containing late transition metals and noble metals (Coordinat. Chem. Rev. 2011, 255, 1642-1685 and Angew. Chem. Int. Ed. 2012, 51, 9492-9510) reveal that, although there is a noticeable development in this area in recent years and decades, the POMs containing noble metals are almost exclusively still based on early transition metals, including Group 5 and 6 metals. Very few of these POMs are solely based on noble metals. In many cases the noble metals are incorporated in structural frameworks primarily composed of early transition metals, including Group 5 and 6 metals.

Thus, there is a need for new POMs containing a major proportion of noble metal atoms, based on the overall metal content of said POMs, and showing useful properties in homogeneous or heterogeneous catalytic applications. In this regard, also those POMs which solely contain noble metals, i.e. which do not contain any other metal atoms than noble metal atoms, and those which contain more than one different type of noble metal atom species are highly promising candidates en route to new, more efficient and more selective catalysts due to the well established unique catalytic properties of noble metals.

Therefore, it is an object of the present invention to provide POMs containing a major proportion of noble metal atoms, based on the overall metal content of said POMs. Furthermore, it is an object of the present invention to provide one or multiple processes for the preparation of said POMs. In addition, it is an object of the present invention to provide supported POMs containing a major proportion of noble metal atoms, based on the overall metal content of said POMs as well as one or multiple processes for the preparation of said supported POMs. Another object of the present invention is the provision of metal-clusters, in particular the provision of highly dispersed metal-cluster particles, and processes for the preparation of said metal-clusters either in the form of a dispersion in a liquid carrier medium or in supported form, immobilized on a solid support. Finally, it is an object of the present invention to provide one or multiple processes for the homogeneous or heterogeneous reductive conversion of organic substrate using said optionally supported POM(s) and/or said optionally supported or dispersed metal-cluster(s).

SUMMARY OF THE INVENTION

An objective of the present invention among others is achieved by the provision of POMs represented by the formula $$(A_n)^{m+}\{M'_s[M''M_{12}X_8O_yR_zH_q]\}^{m-}$$

or solvates thereof, wherein
each A independently represents a cation,
n is the number of cations,
all M are the same, and are selected from the group consisting of Pd, Pt, Rh, Ir, Ag, and Au, and each M has d$^8$ valence electron configuration,
each M' is independently selected from the group consisting of Rh, Ir, Pd, Pt, Ag, Au, Cd, Hg and mixtures thereof,
s is a number from 1 to 8,
M'' is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg and lanthanide metal,
each X is independently selected from the group consisting of Al, Ga, Si, Ge, P, As, Sb, Bi, S, Se, Te and mixtures thereof,
each R is a substituent group which is covalently bonded to X, and each R is independently selected from the group consisting of a hydrogen atom, a substituent group bonded to X via a carbon atom of said substituent group, a substituent group bonded to X via an oxygen atom of said substituent group, a substituent group bonded to X via a sulfur atom of said substituent group, and a substituent group bonded to X via a nitrogen atom of said substituent group,
y is a number from 32 to 40,
z is a number from 0 to 8,
q is a number from 0 to 16, and
m is a number representing the total positive charge m+ of n cations A and the corresponding negative charge m− of the oxo-cluster $\{M'_s[M''M_{12}X_8O_yR_zH_q]\}$.

These noble metal-containing POMs are based on square planar MO$_4$ building blocks. The metal centers of these building blocks have d$^8$ valence electron configuration. Based on the d$^8$ valence electron configuration, the oxidation state of the respective M can be identified, so that M is Pd$^{II}$, Pt$^{II}$, Rh$^{I}$, Ir$^{I}$, Ag$^{III}$ or Au$^{III}$. Hence the requirement for M having a d$^8$ valence electron configuration is synonymous to M being selected from the group consisting of Pd$^{II}$, Pt$^{II}$, Rh$^{I}$, Ir$^{I}$, Ag$^{III}$, and Au$^{III}$.

An objective of the present invention among others is achieved by the provision of a process for the preparation of any one of the POMs provided by the present invention, said process comprising:
(a) reacting at least one source of M, at least one source of M' and at least one source of M'' with at least one X-containing and optionally R-containing starting material to form a salt of the oxo-cluster $\{M'_s[M''M_{12}X_8O_yR_zH_q]\}$ or a solvate thereof,
(b) optionally adding at least one salt of A to the reaction mixture of step (a) to form a POM of formula $(A_n)^{m+}\{M'_s[M''M_{12}X_8O_yR_zH_q]\}^{m-}$ or a solvate thereof, and
(c) recovering the POM or solvate thereof.

An objective of the present invention among others is achieved by the provision of a process for the preparation of any one of the POMs provided by the present invention, said process comprising:
(a1) reacting at least one source of M and at least one source of M'' with at least one X-containing and optionally R-containing starting material to form a salt of the polyanion [M''M$_{12}$X$_8$O$_y$R$_z$H$_q$] or a solvate thereof,
(a2) isolating and optionally purifying the product of step (a1),
(a3) reacting the product of step (a2) with at least one source of M' to form a salt of the oxo-cluster $\{M'_s[M''M_{12}X_8O_yR_zH_q]\}$ or a solvate thereof, (b) optionally adding at least one salt of A to the reaction mixture of step (c) to form a POM of formula $(A_n)^{m+}\{M'_s[M''M_{12}X_8O_yR_zH_q]\}^{m-}$ or a solvate thereof, and (c) recovering the POM or solvate thereof.

An objective of the present invention among others is achieved by the provision of supported POMs comprising any one of the POMs provided by the present invention or prepared according to the present invention, on a solid support.

An objective of the present invention among others is achieved by the provision of a process for the preparation of the supported POMs provided by the present invention, said process comprising the step of contacting any one of the POMs provided by the present invention or prepared according to the present invention, with a solid support.

An objective of the present invention among others is achieved by the provision of metal-clusters of the formula

$$\{M^0{}_s[M''M^0{}_{12}]\}$$

wherein all $M^0$ are the same, and are selected from the group consisting of $Pd^0$, $Pt^0$, $Rh^0$, $Ir^0$, $Ag^0$, and $Au^0$, each $M^0$ is independently selected from the group consisting of $Rh^0$, $Ir^0$, $Pd^0$, $Pt^0$, $Ag^0$, $Au^0$, $Cd^0$, $Hg^0$ and mixtures thereof, s is a number from 1 to 8, and M" is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg and lanthanide metal, and the oxidation state of M" is 0 or greater than 0.

An objective of the present invention among others is achieved by the provision of the metal-clusters provided by the present invention in the form of a dispersion in a liquid carrier medium.

An objective of the present invention among others is achieved by the provision of supported metal-clusters comprising any one of the metal-clusters provided by the present invention immobilized on a solid support.

An objective of the present invention among others is achieved by the provision of a process for the preparation of any one of the metal-clusters provided by the present invention, in the form of a dispersion of said metal-clusters dispersed in a liquid carrier medium, said process comprising the steps of (a) dissolving any one of the POMs provided by the present invention or prepared according to the present invention in a liquid carrier medium, (b) optionally providing additive means to prevent agglomeration of the metal-cluster to be prepared, and (c) subjecting the dissolved POM to chemical or electrochemical reducing conditions sufficient to at least partially reduce said POM into corresponding metal-clusters.

An objective of the present invention among others is achieved by the provision of a process for the preparation of supported metal-clusters, i.e. any one of the metal-clusters provided by the present invention, in the form of metal-clusters immobilized on a solid support, said process comprising the steps of (a) contacting the dispersion of metal-clusters provided by the present invention or prepared according to the present invention, with a solid support, thereby immobilizing at least part of the dispersed metal-clusters onto the support and obtaining supported metal-clusters; and (b) optionally isolating the supported metal-clusters.

An objective of the present invention among others is achieved by the provision of a process for the preparation of supported metal-clusters, i.e. any one of the metal-clusters provided by the present invention, in the form of metal-clusters immobilized on a solid support, said process comprising the steps of (a) subjecting any one of the supported POM provided by the present invention or prepared according to the present invention to chemical or electrochemical reducing conditions sufficient to at least partially reduce said POM into corresponding metal-clusters provided by the present invention; and (b) optionally isolating the supported metal-clusters.

An objective of the present invention among others is achieved by the provision of a process for the homogeneous or heterogeneous reductive conversion of organic substrate comprising contacting said organic substrate under addition of hydrogen with any one of the optionally supported POMs provided by the present invention or prepared according to the present invention, and/or with any one of the optionally dispersed or supported metal-clusters provided by the present invention or prepared according to the present invention.

In the context of the present invention the term noble metal comprises the following elements: Rh, Ir, Pd, Pt, Ag, and Au.

With regard to the present invention the expressions Group 1, Group 2, Group 3 etc. refer to the Periodic Table of the Elements and the expressions 3d, 4d and 5d metals refer to transition metals of respective Periods 4, 5 and 6 of the Periodic Table of the Elements.

With regard to the present invention the term cuboctahedron describes the structural arrangement of the 12 M atoms in $(A_n)^{m+}\{M'_s[M''M_{12}X_8O_yR_zH_q]\}^{m-}$.

With regard to the present invention the term guest atom describes the centrally located M" atom within the cuboctahedron in $(A_n)^{m+}\{M'_s[M''M_{12}X_8O_yR_zH_q]\}^{m-}$.

With regard to the present invention the term peripheral atom(s) describes the M' atom(s) located outside of the cuboctahedron in $(A_n)^{m+}\{M'_s[M''M_{12}X_8O_yR_zH_q]\}^{m-}$.

With regard to the present invention the term polyanion describes the negatively charged structural arrangement without the peripheral M' atom(s) $[M''M_{12}X_8O_yR_zH_q]$.

With regard to the present invention the term oxo-cluster or M'-capped oxo-cluster describes the negatively charged structural arrangement including the peripheral M' atom(s) $\{M'_s[M''M_{12}X_8O_yR_zH_q]\}$.

With regard to the present invention the term metal-cluster describes the structural arrangement $\{M^{0}{}_s[M''M^0{}_{12}]\}$.

With regard to the present invention the term nanocube describes the structural arrangement formed by the M, M" and X atoms $M''M_{12}X_8$.

With regard to the present invention the term immobilizing means to render immobile or to fix the position. In the context of a solid support the term immobilizing describes the adhesion to a surface by means of adsorption, including physisorption and chemisorption. Adsorption is based on interactions between the material to be adsorbed and the surface of the solid support such as van-der-Waals interactions, hydrogen-bonding interactions, ionic interactions, etc.

With regard to the present invention the expression primary particles of POM or POMs primary particles describes isolated particles that contain exactly one negatively charged oxo-cluster $\{M'_s[M''M_{12}X_8O_yR_zH_q]\}$. The POMs primary particles of the present invention are substantially monodispersed particles, i.e. the POMs primary particles have a uniform size, corresponding to the size of one oxo-cluster.

The expression POMs secondary particles describes agglomerates of POMs primary particles.

With regard to the present invention the term supported POM describes POM immobilized on a solid support.

With regard to the present invention the expression primary particles of metal-cluster or metal-cluster primary particles describes isolated particles that contain exactly one metal-cluster $\{M'^o{}_s[M''M^o{}_{12}]\}$. The metal-cluster primary particles of the present invention are substantially monodispersed particles, i.e. the metal-cluster primary particles have a substantially uniform size, corresponding to the size of one metal-cluster. The expression metal-cluster secondary particles describes agglomerates of metal-cluster primary particles.

The particle size of the non-aggregated and aggregated POM, and of the non-aggregated and aggregated metal-cluster, respectively, can be determined by various physical methods known in the art. If the particles are dispersed in a liquid medium, the particle size can be determined by light scattering. If the particles are supported on a solid support, solid state techniques are required for determining the particle size of the supported particles, and to distinguish between primary particles (non-aggregated) and secondary particles (aggregated). Suitable solid state techniques include scanning electron microscopy (SEM), transmission electron microscopy (TEM), powder X-ray diffraction or crystallography (powder XRD), etc. Another suitable technique for determining the particle size is pulsed chemi-/physisorption.

With regard to the present invention the term supported metal-cluster describes metal-clusters immobilized on a solid support.

BRIEF DESCRIPTION OF THE FIGS. 1-6

FIG. 1: Thermogravimetric analysis (TGA) curve of $Na_{10}\{Ag_4[Pd_{13}As_8O_{40}]\}\cdot 36H_2O$ ("Na—Ag$_4$Pd$_{13}$") from 20 to 800° C.

Figure 2A:
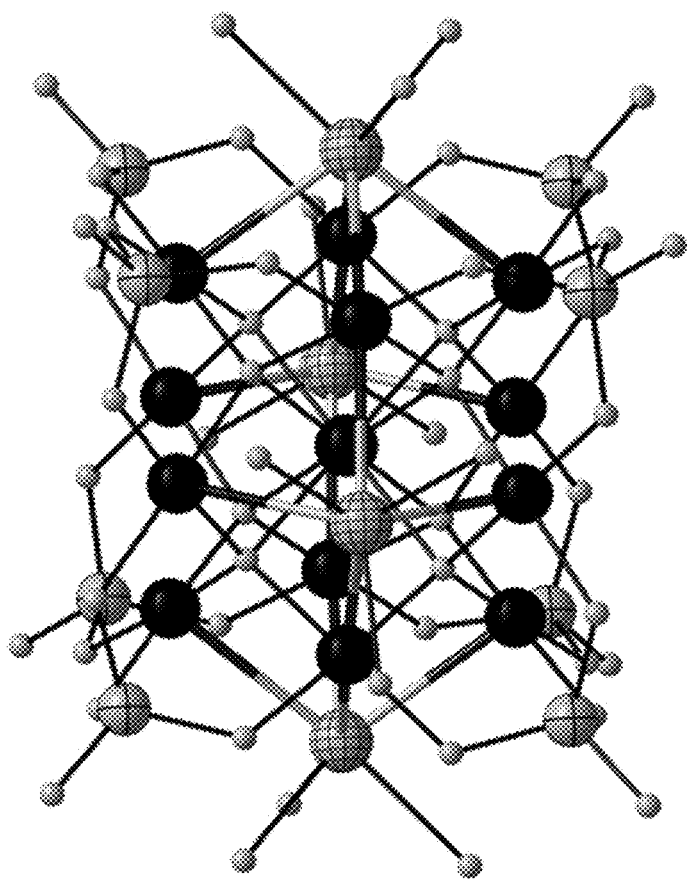
Figure 2B:
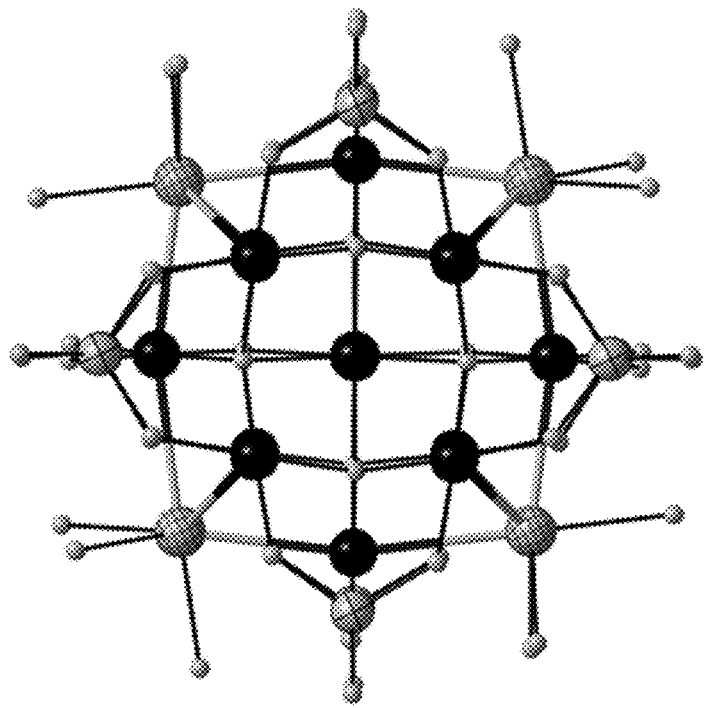

FIG. 2: Ball-and-stick representations of the $\{Ag_4[Pd_{13}As_8O_{40}]\}^{10-}$ oxo-cluster ("Ag$_4$Pd$_{13}$") shown in a view from the side (FIG. 2a) and along the two fold axis (FIG. 2b). Legend: Pd, black spheres; Ag, grey spheres with gridding; As, grey spheres with cross-line; O, grey spheres; Ag—Pd interaction, black-grey bond.

Figure 3B:
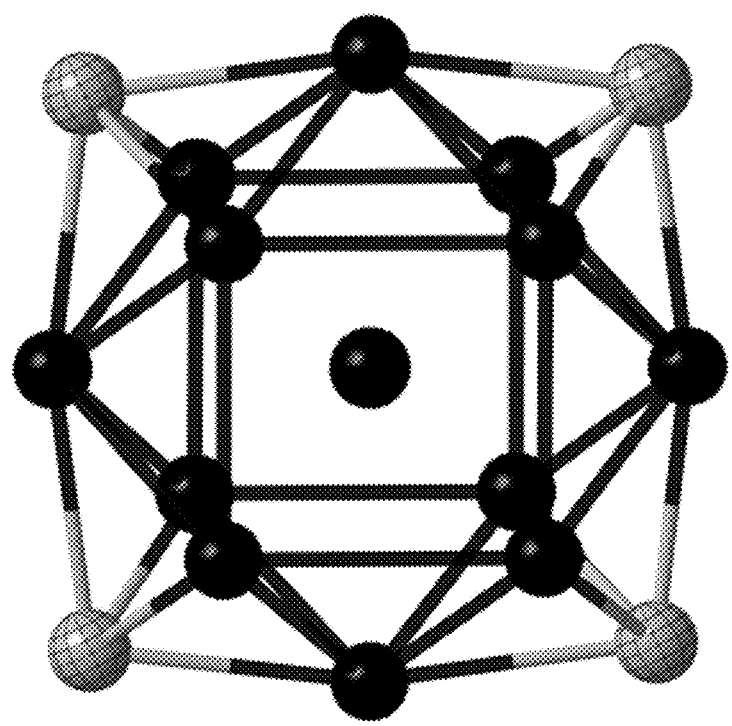
Figure 3A:
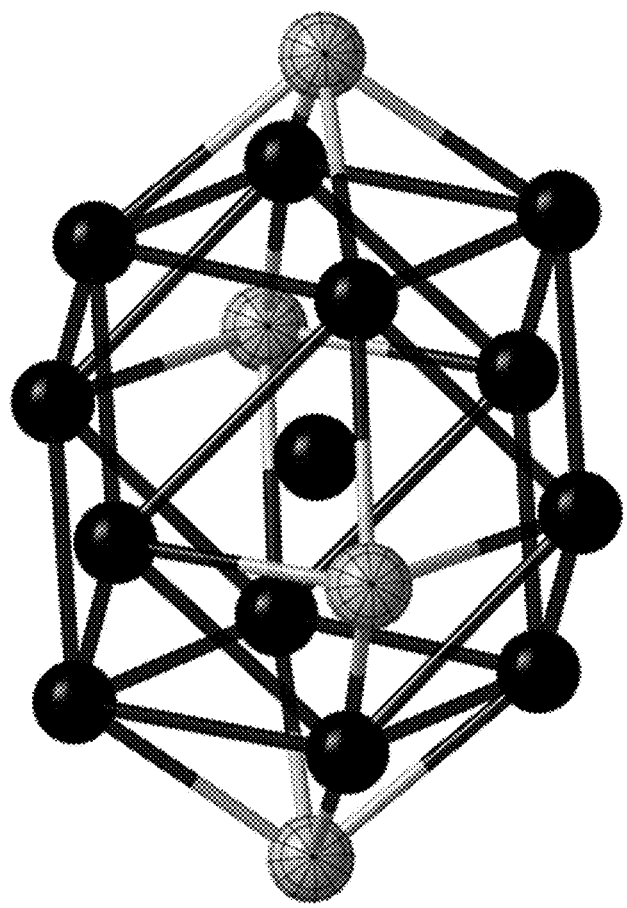

FIG. 3: Pd/Ag skeleton of the $\{Ag_4[Pd_{13}As_8O_{40}]\}^{10-}$ oxo-cluster ("Ag$_4$Pd$_{13}$") in a view from the side (FIG. 3a) and along the two fold axis (FIG. 3b). Legend: Pd, black spheres; Ag, grey spheres with gridding; AgPd interaction, black-grey bond.

Figure 4B:
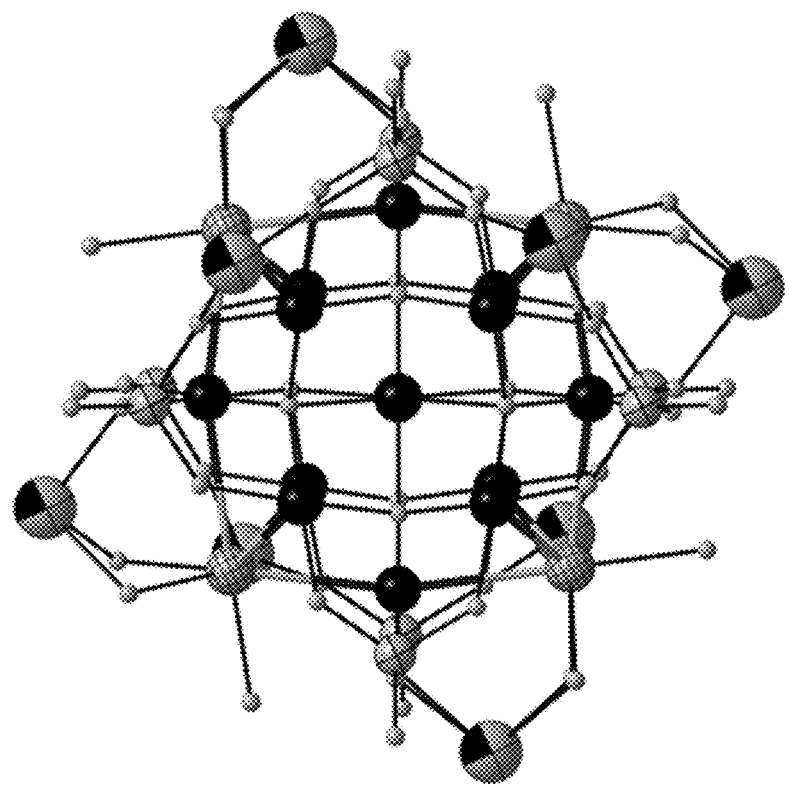
Figure 4A:
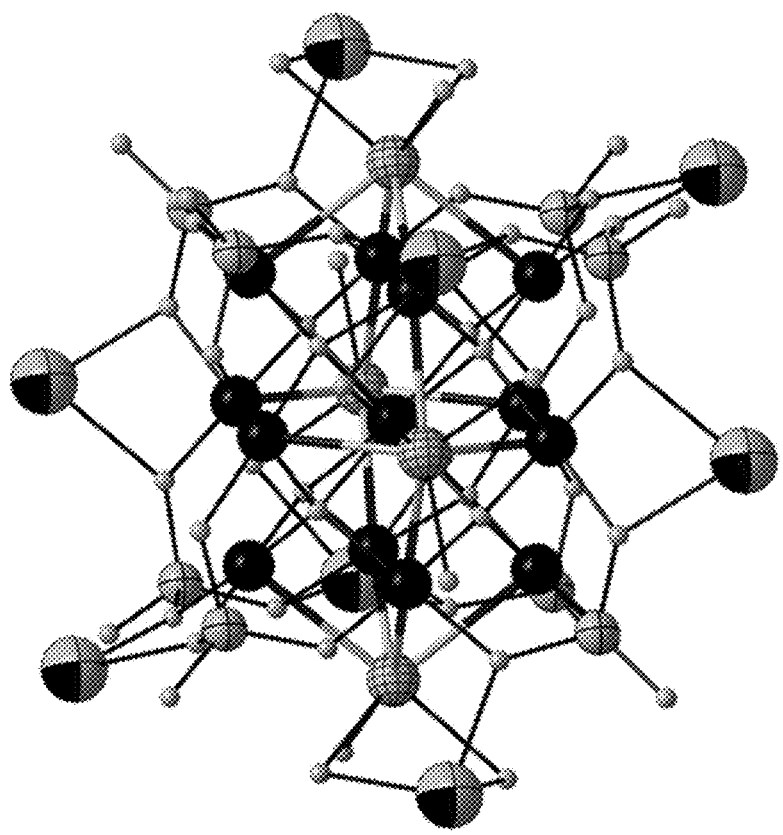

FIG. 4: $\{Ag_4[Pd_{13}As_8O_{40}]\}^{10-}$ oxo-cluster ("Ag$_4$Pd$_{13}$") surrounded by sodium cations in a view from the side (FIG. 4a) and along the two fold axis (FIG. 4b). Legend: Pd, black spheres; Ag, grey spheres with gridding; As, grey spheres with cross-line; Na, black-white spheres; O, grey spheres; AgPd interaction, black-grey bond.

Figure 5:
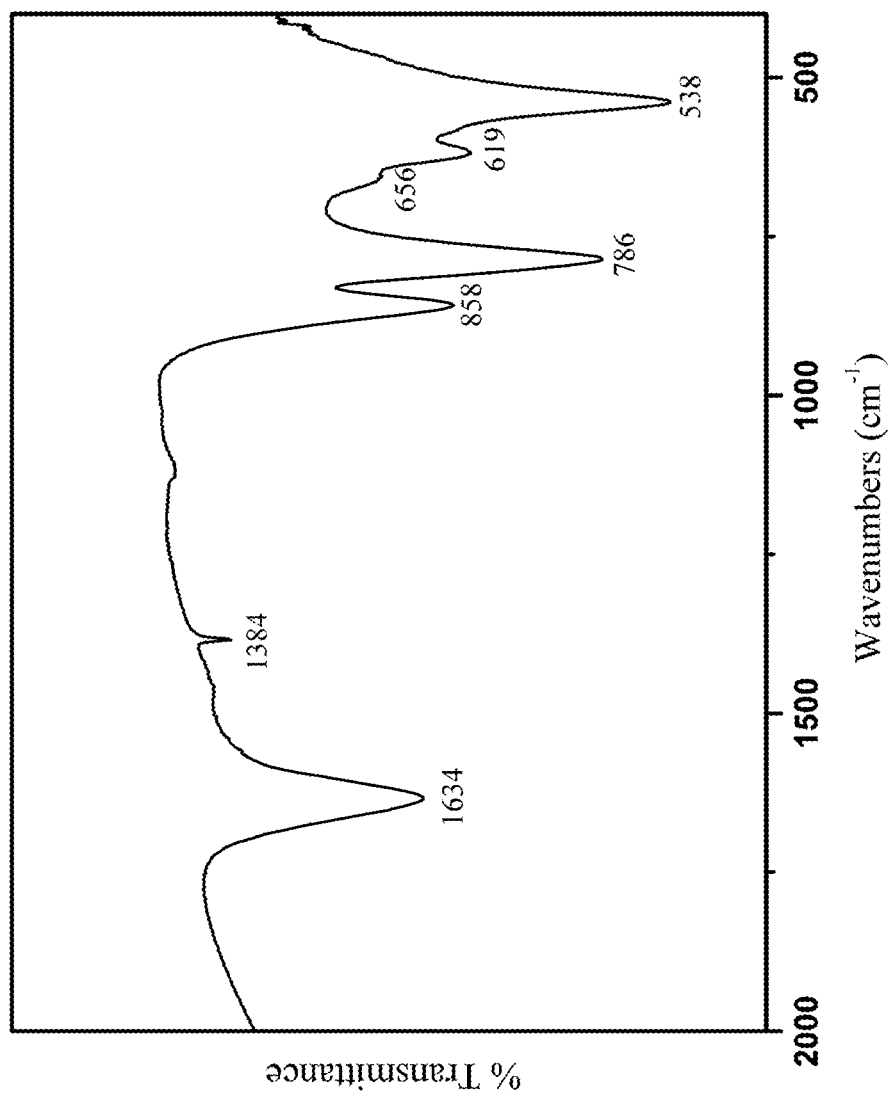

FIG. 5: Fourier Transform Infrared (FT-IR) Spectrum of $Na_{10}\{Ag_4[Pd_{13}As_8O_{40}]\}\cdot 36H_2O$ ("Na—Ag$_4$Pd$_{13}$").

Figure 6:
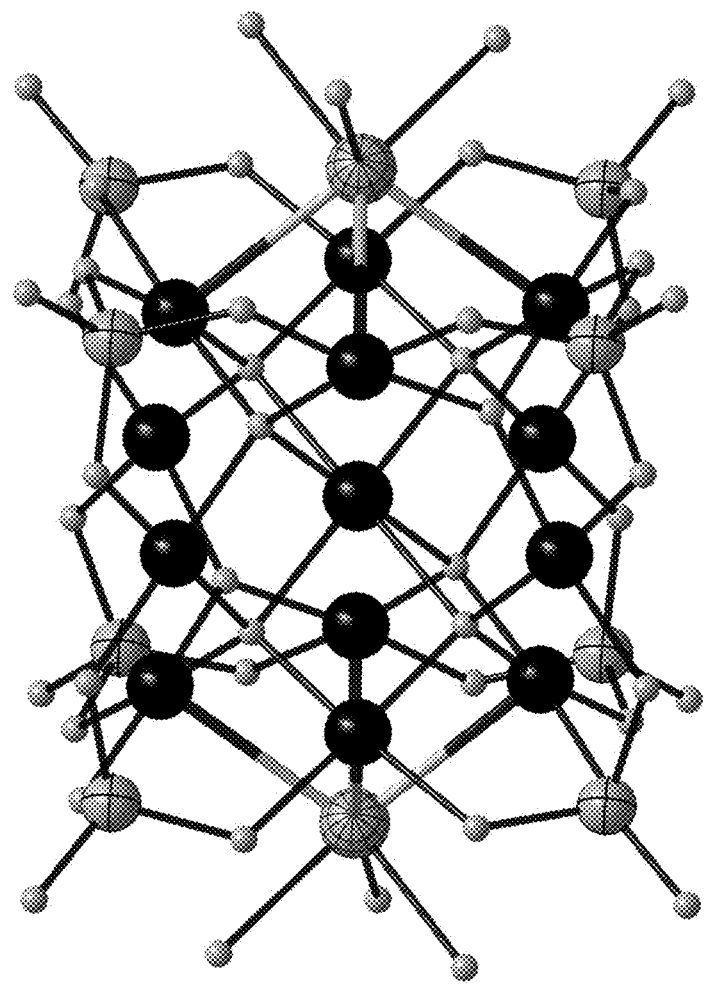

FIG. 6: Ball-and-stick representations of the $\{Ag_2[Pd_{13}As_8O_{40}]\}^{12-}$ oxo-cluster ("Ag$_2$Pd$_{13}$") shown in a view from the side. Legend: Pd, black spheres; Ag, grey spheres with gridding; As, grey spheres with cross-line; O, grey spheres; Ag—Pd interaction, black-grey bond.

DETAILED DESCRIPTION

According to one embodiment, the POMs of the present invention are represented by the formula $$(A_n)^{m+}\{M'_s[M''M_{12}X_8O_y]\}^{m-}$$

or solvates thereof, wherein each A independently represents a cation, preferably each A is independently selected from the group consisting of cations of Li, Na, K, Rb, Cs, Mg, Ca, Sr, Ba, Sc, Ti, V, Cr, Mn, Fe, Co, Ni, Cu, Zn, Y, Zr, Ru, Rh, Pd, Pt, Ag, Cd, Lu, Hf, Re, Os, Ir, Pt, Au, Hg, La, lanthanide metal, actinide metal, Sn, Sb, Te; or phosphonium, ammonium, guanidinium, tetraalkylammonium, protonated aliphatic amines, protonated aromatic amines; or combinations thereof. More preferably, A is selected from lithium, potassium, sodium cations and combinations thereof, n is the number of cations, all M are the same, and are selected from the group consisting of Pd, Pt, Rh, Ir, Ag, and Au, preferably Pd, Pt, Rh, Ir, and Au, more preferably Pd, Pt and Rh, most preferably Pd and Pt, in particular Pd, and each M has d$^8$ valence electron configuration, each M' is independently selected from the group consisting of Rh, Ir, Pd, Pt, Ag, Au, Cd, Hg and mixtures thereof, preferably Rh, Ir, Pd, Pt, Ag, Au and mixtures thereof, more preferably Pd, Pt, Ag, Au and mixtures thereof, most preferably Ag, Au and mixtures thereof, in particular Ag, s is a number from 1 to 8, preferably 2 to 6, more preferably 2 to 4, most preferably 2 or 4, in particular 4, M'' is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg and lanthanide metal, preferably Sr, Sc, Ti, V, Cr, Mn, Fe, Co, Ni, Cu, Zn, Y, Zr, Ru, Rh, Pd, Ag, Cd, Lu, Re, Os, Ir, Pt and Au, more preferably Ti, V, Cr, Mn, Fe, Co, Ni, Cu, Zn, Ru, Rh, Pd, Ag, Re, Os, Ir, Pt and Au, most preferably Rh, Pd, Ag, Ir, Pt and Au, in particular Pd, each X is independently selected from the group consisting of Al, Ga, Si, Ge, P, As, Sb, Bi, S, Se, Te and mixtures thereof, preferably As$^V$, Sb$^V$, Bi$^V$, P$^V$, Si$^{IV}$, Ge$^{IV}$, Al$^{III}$, Ga$^{III}$, S$^{VI}$, Se$^{VI}$, Te$^{VI}$, As$^{III}$, Sb$^{III}$, Bi$^{III}$, Se$^{IV}$, Te$^{IV}$ and mixtures thereof, more preferably As$^V$, Sb$^V$, Bi$^V$, P$^V$, Si$^{IV}$, Ge$^{IV}$, Al$^{III}$, Ga$^{III}$, S$^{VI}$ and mixtures thereof, most preferably As$^V$, Sb$^V$, Bi$^V$, P$^V$ and mixtures thereof, in particular As, preferably As$^V$, y is a number from 32 to 40, preferably 40 or 32, in particular 40, m is a number representing the total positive charge m+ of n cations A and the corresponding negative charge m− of the oxo-cluster $\{M'_s[M''M_{12}X_8O_y]\}$.

According to a second embodiment, the POMs of the present invention are represented by the formula $$(A_n)^{m+}\{M'_s[M''M_{12}X_8O_yR_z]\}^{m-}$$

or solvates thereof, wherein

A, n, m, M, M', M'', s, X and y are the same as defined above, each R is a substituent group which is covalently bonded to X, and each R is independently selected from the group consisting of a hydrogen atom, a substituent group bonded to X via a carbon atom of said substituent group, a substituent group bonded to X via an oxygen atom of said substituent group, a substituent group bonded to X via a sulfur atom of said substituent group, and a substituent group bonded to X via a nitrogen atom of said substituent group, wherein each R may be the same or different; preferably the substituent group R bonded to X via a carbon atom of said substituent group is selected from the group consisting of alkyl, cycloalkyl, alkenyl, cycloalkenyl, alkynyl, and aryl, wherein each of said substituent groups may be unsubstituted or substituted, and each of said substituent groups optionally may contain one or more heteroatoms resulting in hetero-alkyl, hetero-cycloalkyl, hetero-alkenyl, hetero-cycloalkenyl, hetero-alkynyl, and hetero-aryl, and —$CF_3$, —CN, —C(O)$OR^2$, —C(O)$R^2$, and —C(O)$NR^2R^3$; the substituent group R bonded to X via an oxygen atom of said substituent group is selected from the group consisting of —$OR^2$, —O($SO_2$)$R^2$, —O(SO)$R^2$, —O($SO_2$)$OR^2$, —O(SO)$OR^2$, —OS($O_2$)$NR^2R^3$, —OS(O)$NR^2R^3$, —OPO($OR^2$)$_2$, —OPO($OR^2$)$OR^3$, —OPO($R^2$)$OR^3$, —OC(O)$R^2$, —OC(O)$NR^2R^3$, and —OC(O)$OR^2$; the substituent group R bonded to X via a sulfur atom of said substituent group is selected from the group consisting of —$SO_3R^2$, —$SR^2$, —S($O_2$)$R^2$, —S(O)$R^2$, —S(O)$OR^2$, —S(O)$NR^2R^3$, and —S($O_2$)$NR^2R^3$; and the substituent group R bonded to X via a nitrogen atom of said substituent group is selected from the group consisting of —$NR^2R^3$, —N($R^2$)S($O_2$)$R^3$, —N($R^2$)S($O_2$)$NR^3R^4$, —N($R^2$)S($O_2$)$OR^3$, —N($R^2$)S(O)$R^3$, —N($R^2$)S(O)$NR^3R^4$, —N($R^2$)S(O)$OR^3$, —N($R^2$)PO($OR^3$)$_2$, —N($R^2$)PO($OR^3$)$OR^4$, —N($R^2$)PO($R^3$)$OR^4$, —N($R^2$)C(O)$R^3$, —N($R^2$)C(O)$OR^3$, —N($R^2$)C(O)$NR^3R^4$ and —$NO_2$, wherein $R^2$, $R^3$ and $R^4$ are independently selected from the group consisting of H, alkyl, aryl, alkenyl, alkynyl, hetero-alkyl, hetero-cycloalkyl, hetero-alkenyl, hetero-cycloalkenyl, hetero-alkynyl, hetero-aryl and cycloalkyl; more preferably the substituent group R bonded to X via a carbon atom of said substituent group is selected from the group consisting of alkyl, cycloalkyl, and aryl, wherein each of said substituent groups may be unsubstituted or substituted and each of said substituent groups optionally may contain one or more heteroatoms resulting in hetero-alkyl, hetero-cycloalkyl, and hetero-aryl, and —$CF_3$, —C(O)$OR^2$, and —C(O)$NR^2R^3$; the substituent group R bonded to X via an oxygen atom of said substituent group, is selected from the group consisting of —$OR^2$, —O($SO_2$)$R^2$, —O($SO_2$)$OR^2$, —OS($O_2$)$NR^2R^3$, —OPO($OR^2$)$_2$, —OC(O)$R^2$, —OC(O)$NR^2R^3$, and —OC(O)$OR^2$; the substituent group R bonded to X via a sulfur atom of said substituent group, is selected from the group consisting of —$SO_3R^2$, —$SR^2$, —S($O_2$)$R^2$, and —S($O_2$)$NR^2R^3$; and the substituent group R bonded to X via a nitrogen atom of said substituent group is selected from the group consisting of —$NR^2R^3$, —N($R^2$)S($O_2$)$R^3$, —N($R^2$)S($O_2$)$NR^3R^4$, —N($R^2$)S($O_2$)$OR^3$, —N($R^2$)PO($OR^3$)$_2$, —N($R^2$)C(O)$R^3$, —N($R^2$)C(O)$OR^3$, and —N($R^2$)C(O)$NR^3R^4$, wherein $R^2$, $R^3$ and $R^4$ are independently selected from the group consisting of H, alkyl, aryl, hetero-alkyl, hetero-cycloalkyl, hetero-aryl and cycloalkyl; most preferably the substituent group R bonded to X via a carbon atom of said substituent group is selected from the group consisting of alkyl, and aryl, wherein each of said substituent groups may be unsubstituted or substituted and each of said substituent groups optionally may contain one or more heteroatoms resulting in hetero-alkyl, and hetero-aryl, and —C(O)$OR^2$, and —C(O)$NR^2R^3$; the substituent group R bonded to X via an oxygen atom of said substituent group is selected from the group consisting of —$OR^2$, —O($SO_2$)$R^2$, —OC(O)$R^2$, —OC(O)$NR^2R^3$, and —OC(O)$OR^2$; the substituent group R bonded to X via a sulfur atom of said substituent group is selected from the group consisting of —$SR^2$, and —S($O_2$)$R^2$; and the substituent group R bonded to X via a nitrogen atom of said substituent group is selected from the group consisting of —$NR^2R^3$, —N($R^2$)S($O_2$)$R^3$, —N($R^2$)C(O)$R^3$, —N($R^2$)C(O)$OR^3$, and —N($R^2$)C(O)$NR^3R^4$, wherein $R^2$, $R^3$ and $R^4$ are independently selected from the group consisting of H, alkyl, aryl, hetero-alkyl, and hetero-aryl, and z is a number from 0 to 8, preferably 0 or 8, in particular 0.

According to a third embodiment, the POMs of the present invention are represented by the formula

or solvates thereof, wherein

A, n, m, M, M', M'', s, X, y, R and z are the same as defined above, and q is a number from 0 to 16, preferably 0 to 8, more preferably 0 to 6, most preferably 0 or 6.

In a preferred variant of the one, second or third embodiments, all M' are the same, especially all M' are the same and all M' are different from M at the same time.

The polyanion [M''$M_{12}X_8O_yR_zH_q$] of the POMs according to the invention has been found to show structural analogies to the Keggin anion described above. It comprises twelve noble metal atoms M forming a distorted icosahedron (or distorted cuboctahedron) around the thirteenth central guest atom M''. In contrast to other known POMs in which the framework metal atom geometry is distorted octahedral (or more rarely, tetrahedral, square-pyramidal, or seven-coordinated), the 12 noble metal atoms M have a square-planar coordination sphere. The M cations provide a $d^8$ valence electron configuration. In a preferred embodiment, the large positive charge of the M and M'' metal cations is compensated by oxo anions resulting in a M''$M_{12}O_{32}$ assembly having approximately cuboctahedral symmetry.

In a preferred embodiment, the M'-capped oxo-cluster {M'$_s$[M''$M_{12}X_8O_yR_zH_q$]} is composed of classic M''$M_{12}X_8$ nanocubes, with the central M'' being 4 to 8-coordinated, preferably 4, 6 or 8-coordinated, more preferably 4 or 8-coordinated, most preferably 8-coordinated. The oxo-cluster {M'$_s$[M''$M_{12}X_8O_yR_zH_q$]} is surrounded by 1 to 8 M' ions, preferably 2 or 4 equatorial M' ions, more preferably 4 equatorial M' ions. In a preferred embodiment wherein s equals 4, four faces of the nanocube are covered by four M' ions, the four M' ions forming one belt around the M-based nanocube with the top and bottom sides open wherein each M' ion is 7-coordinated, with 4 bonds of M-M' interactions and 3 bonds to terminal water molecules (e.g., FIG. 2). In another embodiment wherein s equals 2, two faces of the nanocube are covered by two M' ions, the two M' ions being located at opposite positions of the M-based nanocube (e.g., FIG. 6). The M-M' distance in the structures, where M' is the same as M, is in a range that provides good proof for the presence of homometallic M-M' interactions. The M-M' distance in the structures, where M' is different from M, is in a range that provides good proof for the presence of heterometallic MM' interactions. In a preferred embodiment the M-M' distance in the structures is in a range from 1.8 to 4.2 Å, more preferably 2.5 to 3.5 Å, most preferably 2.9 to 3.0 Å.

In a preferred embodiment, the framework of the oxo-cluster {M'$_s$[M''$M_{12}X_8O_yR_zH_q$]} can be divided into three parts (e.g., FIG. 3): the central 8-coordinated M" ion encapsulated in the classic $M_{12}$ cuboctahedron and then surrounded by 1 to 8, preferably 2 or 4, more preferably 4, M' ions with M-M' interactions. According to the present invention, none of the X atoms is centrally located. All X atoms are external to the $M_{12}$ cuboctahedron.

In a preferred embodiment, in the solid state, each oxo-cluster is surrounded by n, preferably 1 to 50, more preferably 1 to 30, most preferably 1 to 20 cations A to compensate the charge balance (e.g., FIG. 4), and those cations, together with optional crystal water molecules, isolate the oxo-clusters from each other. The polyanions may be packed in the solid state, so that every two oxo-clusters are connected with each other through 1 to 20, preferably 2 to 10, more preferably 3 to 5, in particular 4 cations A and 1 to 70, preferably 2 to 30, more preferably 5 to 15, in particular 10 water molecules.

In a preferred embodiment, where z equals 0, the eight triangular faces of the $M"M_{12}O_{32}$ cuboctahedron are each capped by a positively charged $XO_p^{v+}$ group to form a distorted cube $M"M_{12}X_8O_y$, such as $M"M_{12}X_8O_{40}$. In a preferred embodiment, in the above $XO_p^{v+}$ group, p is 1 if X is $As^V$, $Sb^V$, $Bi^V$, $P^V$, $Si^{IV}$, $Ge^{IV}$, $Al^{III}$, $Ga^{III}$, $S^{VI}$, $Se^{VI}$ or $Te^{VI}$. In another preferred embodiment p is 0, if X is a heteroatom having a lone pair of electrons, i.e., X is $As^{III}$, $Sb^{III}$, $Bi^{III}$, $Se^{IV}$ or $Te^{IV}$. v is the positive charge of the $XO_p^{v+}$ group and is dependent on the oxidation state of X as well as the number of oxygen atoms p. If p is 1, then v is +1 ($Al^{III}$, $Ga^{III}$), +2 ($Si^{IV}$, $Ge^{IV}$), +3 ($As^V$, $Sb^V$, $Bi^V$, $P^V$) or +4 ($Se^{VI}$, $Te^{VI}$). If p is 0, then v is equal to the oxidation state of X, such as +3 ($As^{III}$, $Sb^{III}$, $Bi^{III}$) or +4 ($Se^{IV}$, $Te^{IV}$). In a preferred embodiment, each of the eight triangular faces of the $M"M_{12}O_{32}$ cuboctahedron can also be capped by a positively charged $XR^{t+}$ group to form a distorted cube $M"M_{12}O_{32}(XR)_8$ wherein X is Al, Ga, Si, Ge, P, As, Sb, Bi, S, Se, Te, preferably $As^V$, $Sb^V$, $Bi^V$, $P^V$, $Si^{IV}$, $Ge^{IV}$, $Al^{III}$, $Ga^{III}$, $S^{VI}$, $Se^{VI}$, $Te^{VI}$, $As^{III}$, $Sb^{III}$, $Bi^{III}$, $Se^{IV}$ and/or $Te^{IV}$, more preferably $As^V$, $P^V$, $Si^{IV}$ and/or $Ge^{IV}$ and R is as defined above such as —H, —$C_6H_5$, —$CH_3$, —$C_2H_5$, —$CH_2COOH$ or —$CH_2NH_2$. t is the positive charge of the $XR^{t+}$ group and is dependent on the oxidation state of X. In a preferred embodiment, if X is $P^V$ or $As^V$, t is +4 and if X is $Si^{IV}$ or $Ge^{IV}$ t is +3. Group R covalently bonded to the heteroatom allows for tuning of (i) the steric and electrostatic parameters on the surface of the POM, and (ii) the solubility properties of the POM ranging from hydrophilic to hydrophobic. Furthermore, if group R is substituted by one or more X-containing moieties, e.g., —$PO_3H_2$, —$AsO_3H_2$, —$SiO_3H_3$ or —$GeO_3H_3$, a POM oxo-cluster can be linked via such X-containing moieties to one or more other POM oxo-clusters, thus, forming chains or networks of POM oxo-clusters.

In a preferred embodiment, each of the eight triangular faces of the $M"M_{12}O_{32}$ cuboctahedron can also be capped by a positively charged X-containing group independently selected from the groups comprising $XR^{t+}$ species and $XO_p^{v+}$ species. In general, if a group R is covalently bonded to X, X is selected preferably from the group consisting of $As^V$, $P^V$, $Si^{IV}$ and/or $Ge^{IV}$.

The POMs of the present invention are in the form of primary and/or secondary particles. In an especially preferred embodiment, the POMs provided by the present invention are mainly in the form of primary particles (i.e. non-agglomerated primary particles), that is at least 90 wt % of the POMs are in the form of primary particles, preferably at least 95 wt %, more preferably at least 99 wt %, in particular substantially all the POMs particles are in the form of primary particles.

The size of the present POMs primary particles has been found to be about 1 $nm^3$ determined by single-crystal X-ray diffraction analysis.

Specific examples of structures of specific POMs of the present invention are also illustrated in FIGS. 2 to 4 and 6.

In comparison to known TMSPs (transition metal-substituted POMs), the present POMs are characterized in that at least a major proportion of the oxo-cluster metal atom positions of the POM framework are occupied by noble metal atoms selected from Rh, Ir, Pd, Pt, Ag, Au, and mixtures thereof. Due to the exceptionally high concentration and accessibility of the noble metal centers in the nanosized molecular entity described herein a unique catalytic performance in reduction reactions is achieved by the POMs of the present invention.

In the POMs of the present invention, the cation A can be a Group 1, 2, 3, 4, 5, 6, 7, 8, 9, 10, 11, 12, 13, 14, 15 and 16 metal cation or an organic cation. Preferably, each A is independently selected from the group consisting of cations of Li, Na, K, Rb, Cs, Mg, Ca, Sr, Ba, Sc, Ti, V, Cr, Mn, Fe, Co, Ni, Cu, Zn, Y, Zr, Ru, Rh, Pd, Pt, Ag, Cd, Lu, Hf, Re, Os, Ir, Pt, Au, Hg, La, lanthanide metal, actinide metal, Sn, Sb, Te; or phosphonium, ammonium, guanidinium, tetraalkylammonium, protonated aliphatic amines, protonated aromatic amines; or combinations thereof. More preferably, A is selected from lithium, potassium, sodium cations and combinations thereof.

The number n of cations is dependent on the nature of cation(s) A, namely its/their valence, and the negative charge m of the oxo-cluster which has to be balanced. In any case, the overall charge of all cations A is equal to the charge of the oxo-cluster. In turn, the charge m of the oxo-cluster is dependent on the nature and oxidation state of the metals M, M' and M", the nature and oxidation state of the heteroatoms X and the number of oxygen atoms y. Thus, m depends on the oxidation state of the atoms present in the oxo-cluster, e.g., it follows from the oxidation states of O (–2), X (ranging from +3 to +6 such as +3 for $Al^{III}$, $Ga^{III}$, $As^{III}$, $Sb^{III}$, $Bi^{III}$, +4 for $Si^{IV}$, $Ge^{IV}$, $Se^{IV}$, $Te^{IV}$, +5 for $As^V$, $Sb^V$, $Bi^V$, $P^V$ or +6 $Se^{VI}$ and $Te^{VI}$), and M, M' and M" (normally ranging from +1 to +3 such as +1 for Ag, Rh and Ir, +2 for Pd and Pt, and +3 for Au). In some embodiments, m ranges from 1 to 43. In particular, m is 6, 9, 10, 14, 22, 30 or 35. In a preferred embodiment, m is 10. Thus, n can generally range from 1 to 43. In particular, n ranges from 6 to 30 and more particularly is 6, 10, 14, 22 or 30. In a preferred embodiment, n is 10.

Generally, A is acting as counterion of the oxo-cluster and is positioned outside of the POM oxo-cluster. However, it is also possible that some of the cations A are located within the POM oxo-cluster.

In contrast, if one or multiple protons are present as counterion(s) in a preferred embodiment, said one or multiple protons are located within the oxo-cluster, and said one or multiple protons can be covalently bonded to oxygen atom(s) of the polyanion with the proviso that no more than one proton is bonded per oxygen. Thus, each proton being located inside a POM oxo-cluster and, preferably, being bonded to one or more of the atoms of the polyanion framework, is represented by one of q protons of the oxo-cluster $\{M'_s[M"M_{12}X_8O_yR_zH_q]\}$. Generally, q is ranging from 0 to 16. In particular, q is 0 or 6. In a preferred embodiment q is 0, i.e. no group H is present. In another embodiment q is 1, 2, 3, 4, 5, 6, 7, 8, 9, 10, 11, 12, 13, 14, 15, or 16. In a preferred embodiment of the present invention the q protons are bonded to oxygen atoms of the polyanion framework, with the proviso that each of said protons is bonded to a different oxygen atom of the polyanion framework. Thus, in this specific preferred embodiment the POM is best represented by the formulae

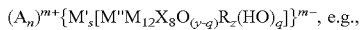, e.g.,

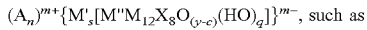, such as

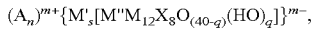, or solvates thereof, wherein A, n, m, M, M', M", s, X, y, R, z and q are the same as defined above.

The M atoms have a square-planar coordination sphere, and they provide a $d^8$ valence electron configuration. Preferably M is selected from $Pt^{II}$ or $Pd^{II}$, most preferably M is $Pd^{II}$. Preferably M" is Pd, most preferably $Pd^{11}$. Preferably all M' are the same. Preferably all M' are different from M. In a most preferred embodiment, all M' are the same, and all M' are different from M at the same time. Preferably M' is selected from Ag or Au, most preferably M' is Ag. Preferably X is selected from P, As, Sb or Bi, most preferably X is As. Preferably s is 2 or 4, more preferably s is 4, and most preferably z and q are 0.

In another embodiment each R is a substituent group which is covalently bonded to X, and R is hydrogen or a substituent group wherein each R that is not hydrogen provides an oxygen atom, a carbon atom, a sulfur atom or a nitrogen atom for coordination to the X atom within the polyanion $[M''M_{12}X_8O_yR_zH_q]$, wherein each R may be the same or different, preferably R is hydrogen or a substituent group wherein each R that is not hydrogen provides an oxygen atom, a carbon atom, a sulfur atom or a nitrogen atom for coordination to the X atom and wherein each R that is not hydrogen comprises one or more moieties independently selected from the group consisting of H, alkyl, alkenyl, alkynyl, aryl, heteroaryl, cycloalkyl, heterocycloalkyl, aryalkyl, arylalkenyl, cycloalkylalkyl, heterocycloalkylalkyl and heteroarylalkyl, wherein each of said alkyl, alkenyl, alkynyl, aryl, heteroaryl, cycloalkyl and heterocycloalkyl can be unsubstituted or substituted with one or more moieties which can be the same or different, each of said moieties being independently selected from the group consisting of halogen, alkyl, alkenyl, alkynyl, aryl, heteroaryl, cycloalkyl, heterocycloalkyl, arylalkyl, arylalkenyl, cycloalkylalkyl, heterocycloalkylalkyl, heteroarylalkyl, —$CF_3$, —CN, —$OR^2$, —$NR^2R^3$, —$C(O)OR^2$, —$C(O)R$, —$C(O)NR^2R^3$, —$SO_3H$, —$SR^2$, —$S(O_2)R^2$, —$S(O_2)NR^2R^3$, —$N(R^2)S(O_2)R^3$, —$N(R^2)C(O)R^3$, —$N(R^2)C(O)NR^2R^3$, —$NO_2$, and X-containing moieties through which a POM oxo-cluster can be linked to one or more other POM oxo-clusters, each of $R^2$ and $R^3$ being selected from the group consisting of H, alkyl, aryl, alkenyl, alkynyl, heteroalkyl, hetero-cycloalkyl, hetero-alkenyl, hetero-cycloalkenyl, hetero-alkynyl, hetero-aryl and cycloalkyl.

In general, R is hydrogen or an unsubstituted or substituted group, preferably an unsubstituted or substituted organic group, as defined in this specification. As used herein, "alkyl" represents a straight or branched aliphatic hydrocarbon group with 1 to about 20 carbon atoms. Preferred alkyl groups contain 1 to about 12 carbon atoms. More preferred alkyl groups contain 1 to about 6 carbon atoms. Non-limiting examples of suitable alkyl groups include methyl, ethyl, n-propyl, isopropyl and t-butyl. "Alkenyl" represents a straight or branched aliphatic hydrocarbon group containing at least one carbon-carbon double bond and having 2 to about 15 carbon atoms. Preferred alkenyl groups have 2 to about 12 carbon atoms; and more preferably 2 to about 4 carbon atoms. Non-limiting examples of suitable alkenyl groups include ethenyl, propenyl and 2-butenyl. "Alkynyl" represents a straight or branched aliphatic hydrocarbon group containing at least one carbon-carbon triple bond and having 2 to about 15 carbon atoms. Preferred alkynyl groups have 2 to about 12 carbon atoms; and more preferably 2 to about 4 carbon atoms in the chain. Non-limiting examples of suitable alkynyl groups include ethynyl, propynyl, 2-butynyl and 3-methylbutynyl. "Aryl" represents an aromatic monocyclic or multicyclic ring system comprising about 6 to about 14 carbon atoms, preferably about 6 to about 10 carbon atoms. Non-limiting examples of suitable aryl groups include phenyl and naphthyl. "Heteroaryl" represents an aromatic monocyclic or multicyclic ring system comprising about 5 to about 14 ring atoms, preferably about 5 to about 10 ring atoms, in which one or more of the ring atoms is an element other than carbon, for example, nitrogen, oxygen or sulfur, alone or in combination. Preferred heteroaryls contain about 5 to about 6 ring atoms. Non-limiting examples of suitable heteroaryls include pyridyl, pyrazinyl, furanyl, thienyl, pyrimidinyl, pyridine (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. "Cycloalkyl" represents a non-aromatic mono- or multicyclic ring system comprising 3 to about 10 carbon atoms, preferably about 5 to about 10 carbon atoms. Preferred cycloalkyl rings contain about 5 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like. "Heterocyclyl" represents a non-aromatic saturated monocyclic or multicyclic ring system comprising 3 to about 10 ring atoms, preferably about 5 to about 10 ring atoms, in which one or more of the atoms in the ring system is an element other than carbon, for example, nitrogen, oxygen or sulfur, alone or in combination. Preferred heterocyclyls contain about 5 to about 6 ring atoms. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Arylalkyl" represents an aryl-alkyl-group in which the aryl and alkyl are as previously described. Non-limiting examples of suitable arylalkyl groups include benzyl, 2-phenethyl and naphthalenylmethyl. The bond to X is through the alkyl. Likewise, also "cycloalkylalkyl", "heterocyclylalkyl" and "heteroarylalkyl" are bound to X via the alkyl. In preferred embodiments, R is H, —$CH_3$, —$C_2H_5$, —$C_3H_7$, —$C_4H_9$, —$C_6H_5$, —$CH_2COOH$, —$CH_2NH_2$, —$CH_2CH_2COOH$, —$CH_2CH_2Cl$, —$CH_2CH_2CH(NH_2)COOH$, -(p-$C_6H_4NH_2$), -(p-$C_6H_4NO_2$), -(p-$C_6H_4OH$) or 3-nitro-4-hydroxy phenyl.

Generally, z is ranging from 0 to 8. In particular, z is 0 or 8. In a preferred embodiment z is 0, i.e. no group R is present. In another embodiment z is 1, 2, 3, 4, 5, 6, 7, or 8.

The number of oxygen atoms y depends on the nature of the heteroatoms X and the number z of groups R present in the POM. In a preferred embodiment, if z is 0 and X is $As^V$, $Sb^V$, $Bi^V$, $P^V$, $Si^{IV}$, $Ge^{IV}$, $Al^{III}$, $Ga^{III}$, $S^{VI}$, $Se^{VI}$ or $Te^{VI}$ then y is 40. In another preferred embodiment, if z is 0 and X is $As^{III}$, $Sb^{III}$, $Bi^{III}$, $Se^{IV}$ or $Te^{IV}$, then y is 32. In another preferred embodiment, if z is 8, then X is preferably $As^V$, $P^V$, $Si^{IV}$ and $Ge^{IV}$ and y is 32.

Thus, in a preferred embodiment the invention relates to a POM $(A_n)^{m+}\{M'_s[M''M_{12}X_8O_yR_zH_q]\}^{m-}$, wherein M'' is Pd.

Thus, in a preferred embodiment the invention relates to a POM $(A_n)_{m+}\{M'_s[M''M_{12}X_8O_yR_zH_q]\}^{m-}$, wherein M is $Pd^{II}$, M' is Ag, X is As, and s is 2 or 4.

Thus, in a preferred embodiment the invention relates to a POM $(A_n)^{m+}\{M'_s[M''M_{12}X_8O_yR_zH_q]\}^{m-}$, wherein M is $Pd^{II}$, M' is Ag, X is As, and s is 2 or 4, wherein all M' are the same, and all M' are different from M.

Thus, in a preferred embodiment the invention relates to a POM $(A_n)^{m+}\{M'_s[M''M_{12}X_8O_yR_zH_q]\}^{m-}$, wherein M is $Pd^{II}$, M'' is Pd, M' is Ag, X is As, and s is 2 or 4.

Accordingly, in a preferred embodiment the invention relates to POMs represented by the formulae $(A_n)^{10+}\{Ag_4[Pd_{13}As_8O_{40}]\}^{10-}$ or $(A_n)^{12+}\{Ag_2[Pd_{13}As_8O_{40}]\}^{12-}$ or solvates thereof, wherein A and n are the same as defined above.

Further, suitable examples of POMs according to the invention are represented by the formulae $(A_n)^{m+}\{M'_s[M''M_{12}X_8O_yR_zH_q]\}^{m-}$, e.g., $(A_n)^{m+}\{M'_s[M''M_{12}X_8O_yH_q]\}^{m-}$, $(A_n)^{m+}\{M'_s[M''M_{12}X_8O_yR_z]\}^{m-}$, $(A_n)^{m+}\{M'_s[M''M_{12}X_8O_y]\}^{m-}$, $(A_n)^{m+}\{M'_s[M''Pd_{12}X_8O_yR_zH_q]\}^{m-}$, $(A_n)^{m+}\{M'_s[M''Pd_{12}X_8O_y]\}^{m-}$, $(A_n)^{m+}\{M'_s[M''Pd_{12}X_8O_{40}]\}^{m-}$, $(A_n)^{10+}\{M'_s[M''Pd_{12}X_8O_{40}]\}^{10-}$, or $(A_n)^{4+}\{M'_s[M''Pd_{12}X_8O_{34}(HO)_6]\}^{4-}$, $(A_{10})^{10+}\{M'_s[M''Pd_{12}X_8O_{40}]\}^{10-}$, $(A_n)^{m+}\{M'_s[Pd_{13}X_8O_yR_zH_q]\}^{m-}$, such as $(A_n)^{m+}\{M'_s[Pd_{13}X_8O_y]\}^{m-}$, $(A_n)^{m+}\{M'_s[Pd_{13}X_8O_{40}]\}^{m-}$, $(A_n)^{10+}\{M'_s[Pd_{13}X_8O_{40}]\}^{10-}$, or $(A_n)^{4+}\{M'_s[Pd_{13}X_8O_{34}(HO)_6]\}^{4-}$, $(A_{10})^{10+}\{M'_s[Pd_{13}X_8O_{40}]\}^{10-}$, $(A_n)^{m+}\{Ag_s[Pd_{13}X_8O_yR_zH_q]\}^{m-}$, such as $(A_n)^{m+}\{Ag_s[Pd_{13}X_8O_y]\}^{m-}$, $(A_n)^{m+}\{Ag_s[Pd_{13}X_8O_{40}]\}^{m-}$, $(A_n)^{10+}\{Ag_s[Pd_{13}X_8O_{40}]\}^{10-}$, or $(A_n)^{4+}\{Ag_s[Pd_{13}X_8O_{34}(HO)_6]\}^{4-}$, $(A_{10})^{10+}\{Ag_s[Pd_{13}X_8O_{40}]\}^{10-}$, $(A_n)^{m+}\{Ag_4[Pd_{13}X_8O_yR_zH_q]\}^{m-}$, such as $(A_n)^{m+}\{Ag_4[Pd_{13}X_8O_y]\}^{m-}$, $(A_n)^{m+}\{Ag_4[Pd_{13}X_8O_{40}]\}^{m-}$, $(A_n)^{10+}\{Ag_4[Pd_{13}X_8O_{40}]\}^{10-}$, or $(A_n)^{4+}\{Ag_4[Pd_{13}X_8O_{34}(HO)_6]\}^{4-}$, $(A_{10})^{10+}\{Ag_4[Pd_{13}X_8O_{40}]\}^{10-}$, $(A_n)^{m+}\{Ag_4[Pd_{13}As_8O_yR_zH_q]\}^{m-}$, such as $(A_n)^{m+}\{Ag_4[Pd_{13}As_8O_y]\}^{m-}$, $(A_n)^{m-}\{Ag_4[Pd_{13}As_8O_{40}]\}^{m-}$, $(A_n)^{10+}\{Ag_4[Pd_{13}As_8O_{40}]\}^{10-}$, or $(A_n)^{4+}\{Ag_4[Pd_{13}As_8O_{34}(HO)_6]\}^{4-}$, $(A_{10})^{10+}\{Ag_4[Pd_{13}As_8O_{40}]\}^{10-}$, $(Na_{10})^{10+}\{Ag_4[Pd_{13}As_8O_{40}]\}^{10-}$, or $(Na_4)^{4+}\{Ag_4[Pd_{13}As_8O_{34}(HO)_6]\}^{4-}$, $(A_n)^{10+}\{Au_4[Pd_{13}As_8O_{40}]\}^{10-}$, or $(A_n)^{4+}\{Au_4[Pd_{13}As_8O_{34}(HO)_6]\}^{4-}$, $(A_n)^{10+}\{Ag_4[Pd_{13}P_8O_{40}]\}^{10-}$, or $(A_n)^{4+}\{Ag_4[Pd_{13}P_8O_{34}(HO)_6]\}^{4-}$, $(A_n)^{10+}\{Ag_4[Pt_{13}As_8O_{40}]\}^{10-}$, or $(A_n)^{4+}\{Ag_4[Pt_{13}As_8O_{34}(HO)_6]\}^{4-}$, and $(A_n)^{10+}\{Pd_4[Pd_{13}As_8O_{40}]\}^{10-}$, or $(A_n)^{4+}\{Pd_4[Pd_{13}As_8O_{34}(HO)_6]\}^{4-}$, $(A_n)^{m+}\{Ag_2[Pd_{13}X_8O_yR_zH_q]\}^{m-}$, such as $(A_n)^{m+}\{Ag_2[Pd_{13}X_8O_y]\}^{m-}$, $(A_n)^{m+}\{Ag_2[Pd_{13}X_8O_{40}]\}^{m-}$, $(A_n)^{12+}\{Ag_2[Pd_{13}X_8O_{40}]\}^{12-}$, or $(A_n)^{m+}\{Ag_2[Pd_{13}As_8O_yR_zH_q]\}^{m-}$, such as $(A_n)^{m+}\{Ag_2[Pd_{13}As_8O_y]\}^{m-}$, $(A_n)^{m+}\{Ag_2[Pd_{13}As_8O_{40}]\}^{m-}$, $(A_n)^{12+}\{Ag_2[Pd_{13}As_8O_{40}]\}^{12-}$, or $(Na_x)^{12+}\{Ag_4[Pd_{13}As_8O_{40}]\}^{12-}$, or $(A_n)^{12+}\{Ag_2[Pd_{13}P_8O_{40}]\}^{12-}$, or $(A_n)^{12+}\{Ag_2[Pt_{13}As_8O_{40}]\}^{12-}$.

The invention also includes solvates of the present POMs. A solvate is an association of solvent molecules with a POM.

Preferably, water is associated with the POMs and thus, the POMs according to the invention can in particular be represented by the formulae $(A_n)^{m+}\{M'_s[M''M_{12}X_8O_yR_zH_q]\}^{m-}\cdot wH_2O$, e.g., $(A_n)^{m+}\{M'_s[M''M_{12}X_8O_y]\}^{m-}\cdot wH_2O$, $(A_n)^{m+}\{M'_s[M''M_{12}X_8O_{40}]\}^{m-}\cdot wH_2O$, or $(A_n)^{m+}\{M'_s[M''M_{12}X_8O_{(40-q)}(HO)_q]\}^{m-}\cdot wH_2O$, and $(A_n)^{m+}\{Ag_4[M''Pd_{12}X_8O_{(40-q)}(HO)_q]\}^{m-}\cdot wH_2O$, or $(A_n)^{m+}\{Ag_2[M''Pd_{12}X_8O_{(40-q)}(HO)_q]\}^{m-}\cdot wH_2O$, wherein
A, n, m, M, M', M", s, X, y, R, z and q are the same as defined above, and
w represents the number of attracted water molecules per POM oxo-cluster and mostly depends on the type of cations A. In some embodiments w is an integer from 1 to 100, preferably 1 to 80, more preferably 10 to 60, most preferably 20 to 50 such as 36.

Suitable examples of the POM solvates according to the invention are represented by the formulae $(A_n)^{m+}\{M'_s[M''Pd_{12}X_8O_{40}]\}^{m-}\cdot wH_2O$, e.g., $(A_n)^{m+}\{Ag_s[M''Pd_{12}X_8O_{40}]\}^{m-}\cdot wH_2O$, $(A_n)^{m+}\{Ag_4[M''Pd_{12}X_8O_{40}]\}^{m-}\cdot wH_2O$, $(A_n)^{m+}\{Ag_2[M''Pd_{12}X_8O_{40}]\}^{m-}\cdot wH_2O$, $(A_n)^{m+}\{M'_s[Pd_{13}X_8O_{40}]\}^{m-}\cdot wH_2O$, $(A_n)^{m+}\{M'_s[Pd_{13}As_8O_{40}]\}^{m-}\cdot wH_2O$, $(A_n)^{m+}\{M'_s[M''M_{12}X_8O_{(y-q)}(HO)_q]\}^{m-}\cdot wH_2O$ and $(A_n)^{m+}\{M'_s[M''M_{12}X_8O_{(40-q)}(HO)_q]\}^{m-}\cdot wH_2O$, such as $(A_n)^{m+}\{Ag_4[M''Pd_{12}As_8O_{40}]\}^{m-}\cdot wH_2O$, $(A_n)^{m+}\{Au_4[M''Pd_{12}As_8O_{40}]\}^{m-}\cdot wH_2O$, $(A_n)^{m+}\{Ag_4[Pd_{13}As_8O_{40}]\}^{m-}\cdot wH_2O$, $(A_n)^{10+}\{Ag_4[Pd_{13}As_8O_{40}]\}^{10-}\cdot wH_2O$, $(Na_{10})^{10+}\{Ag_4[Pd_{13}As_8O_{40}]\}^{10-}\cdot 36H_2O$, $(A_n)^{m+}\{Ag_4[PdM_{12}As_8O_{(y-q)}(HO)_q]\}^{m-}\cdot wH_2O$ $(A_n)^{m+}\{Ag_4[M''Pd_{12}As_8O_{34}(HO)_6]\}^{m-}\cdot 36H_2O$, $(A_n)^{m+}\{Ag_2[M''Pd_{12}As_8O_{40}]\}^{m-}\cdot wH_2O$, $(A_n)^{m+}\{Au_2[M''Pd_{12}As_8O_{40}]\}^{m-}\cdot wH_2O$, $(A_n)^{m+}\{Ag_2[Pd_{13}As_8O_{40}]\}^{m-}\cdot wH_2O$, $(A_n)^{12+}\{Ag_2[Pd_{13}As_8O_{40}]\}^{12-}\cdot wH_2O$, and $(A_n)^{m+}\{Ag_2[PdM_{12}As_8O_{(y-q)}(HO)_q]\}^{m-}\cdot wH_2O$.

In a preferred embodiment, water molecules, if present at all, are coordinated to M', protons and/or A cations, while the M and M" cations are not coordinated by water. In a preferred embodiment, a proportion of the water molecules is not directly attached to the POM framework $(A_n)^{m+}\{M'_s[M''M_{12}X_8O_yR_zH_q]\}^{m-}$ by coordination but rather indirectly by hydrogen-bonding as water of crystallization. Thus, in a preferred embodiment, the attracted water molecules, if present at all, are coordinated to M' and/or A cations and/or possibly exhibit weak interactions by hydrogen bonding to protons of the POM and/or the attracted water molecules, if present at all, are water of crystallization.

The guest atom M" cannot be replaced or removed without destroying the structural framework of the oxo-cluster, once the polyanion framework is formed.

In another embodiment, the POMs may be further calcined at a temperature not exceeding the transformation temperature of the POM, i.e. the temperature at which decomposition of the POM starts to take place (usually about 600-700° C. for the present POMs according to their corresponding TGA). Thus, in a preferred embodiment the POMs of the present invention are thermally stable up to temperatures of around 600-700° C. For the calcination, common equipment may be used, that is commercially available. Calcination of the POMs may be conducted under an oxygen containing gas such as air, under vacuum, under hydrogen or under an inert gas such as argon or nitrogen, more preferably under inert gas, most preferably under nitrogen. Calcination may help to activate a POM pre-catalyst by forming active sites. Upon heating, POM salts first loose water molecules (of water of crystallization) and then organic groups (if present) before they start to transform/decompose, e.g. by oxidation. TGA can be used to study the weight loss of the POM salts, and Differential Scanning calorimetry (DSC) indicates if each step is endo- or exothermic. Such measurements may be carried out e.g. under nitrogen gas, air, oxygen or hydrogen.

In many cases, however, and in particular if the POM is used as a catalyst or pre-catalyst under reductive conditions, drying of the POM without calcination may be sufficient.

The invention is further directed to processes for preparing POMs according to the invention. A first process for preparing POMs according to the present invention is a "one-pot process" comprising:
(a) reacting at least one source of M, at least one source of M' and at least one source of M" with at least one X-containing and optionally R-containing starting material to form a salt of the oxo-cluster $\{M'_s[M''M_{12}X_8O_yR_zH_q]\}$ or a solvate thereof,
(b) optionally adding at least one salt of A to the reaction mixture of step (a) to form a POM of formula $(A_n)^{m+}\{M'_s[M''M_{12}X_8O_yR_zH_q]\}^{m-}$ or a solvate thereof, and
(c) recovering the POM or solvate thereof,
wherein A, n, m, M, M', M", s, X, y, R, z and q are the same as defined above.

Within the spirit and scope of the present invention the term "one-pot process" is used to describe the specific one-pot process described herein, vide supra.

A second process for preparing POMs according to the present invention is a "two-pot process" comprising:
(a1) reacting at least one source of M and at least one source of M" with at least one X-containing and optionally R-containing starting material to form a salt of the polyanion $[M''M_{12}X_8O_yR_zH_q]$ or a solvate thereof,
(a2) isolating and optionally purifying the product of step (a1),
(a3) reacting the product of step (a2) with at least one source or multiple sources of M' to form a salt of the oxo-cluster $\{M'_s[M''M_{12}X_8O_yR_zH_q]\}$ or a solvate thereof, (b) optionally adding at least one salt of A to the reaction mixture of step (a3) to form a POM of formula $(A_n)^{m+}\{M'_s[M''M_{12}X_8O_yR_zH_q]\}^{m-}$ or a solvate thereof, and (c) recovering the POM or solvate thereof.

wherein A, n, m, M, M', M", s, X, y, R, z and q are the same as defined above.

Within the spirit and scope of the present invention the term "two-pot process" is used to describe the specific two-pot process described herein, vide supra. With regard to the present invention step (a) of the two-pot process comprises steps (a1), (a2) and (a3).

In step (a) of the one-pot process and in step (a1) of the two-pot process, at least one source of M" is used, especially one source of M". Generally, in a preferred embodiment of the present invention, salts of the following metals Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg and lanthanide metal such as chlorides, fluorides, hydroxides, nitrates, acetates and/or sulfates can be used as source for M". More preferably, if M" is Pd, $Pd(CH_3COO)_2$, $PdCl_2$, $Pd(NO_3)_2$ and/or $PdSO_4$ are used; if M" is Pt, $PtCl_2$ is used; if M" is Ag, $AgNO_3$, AgF and/or AgCl are used; if M" is gold, $AuCl_3$, $Au(OH)_3$ and/or $HAuCl_4$.aq are used; if M" is Rh, $[(C_6H_5)_3P]_2RhCl(CO)$ and/or $[Rh(CO)_2Cl]_2$ are used; if M" is Ir, $[(C_6H_5)_3P]_2IrCl(CO)$ is used.

In step (a) of the one-pot process and in step (a1) of the two-pot process at least one source of M is used, especially one source of M. Generally, in a preferred embodiment of the present invention, $Pd^{II}$ salts such as $PdCl_2$, $Pd(CH_3COO)_2$, $Pd(NO_3)_2$ and $PdSO_4$, $Pt^{II}$ salts such as $PtCl_2$, $Rh^I$ salts such as $[(C_6H_5)_3P]_2RhCl(CO)$ and $[Rh(CO)_2Cl]_2$, salts such as $[(C_6H_5)_3P]_2IrCl(CO)$, $Au^{III}$ salts such as $AuCl_3$, $Au(OH)_3$ and $HAuCl_4$.aq and $Ag^{III}$ salts preferably generated with oxidizing reagents from $Ag^I$ salts such as $AgNO_3$, AgF and AgCl can be used as source for the noble metal M atoms. More preferably, the $Pd^{II}$ source is $PdCl_2$ or $Pd(CH_3COO)_2$ and the $Pt^{II}$ source is $PtCl_2$.

In step (a) of the one-pot process and in step (a3) of the two-pot process at least one source of M' is used. Generally, in a preferred embodiment of the present invention, Pd salts such as $PdCl_2$, $Pd(CH_3COO)_2$, $Pd(NO_3)_2$, $PdSO_4$, Pt salts such as $PtCl_2$, Rh salts such as $[(C_6H_5)_3P]_2RhCl(CO)$ and $[Rh(CO)_2Cl]_2$, Ir salts such as $[(C_6H_5)_3P]_2IrCl(CO)$, Au salts such as $AuCl_3$, $Au(OH)_3$, $HAuCl_4$.aq, Ag salts such as $AgNO_3$, AgF, AgCl, Cd salts such as $Cd(CH_3COO)_2$, $CdCl_2$, $Cd(NO_3)_2$, $CdSO_4$ and/or Hg salts such as $HgCl_2$, $Hg(NO_3)_2$ can be used as sources for the metal M' atoms. More preferably, $AgNO_3$, $AuCl_3$, $HgCl_2$ and/or $PtCl_2$ are used.

In step (a) of the one-pot process and in step (a1) of the two-pot process the metal source or metal sources are reacted with at least one X-containing starting material. For instance, an oxide of X or an oxo acid of X may be used as X-containing starting material. It is also possible to use a water-soluble salt such as a halide of X. In a preferred embodiment of the present invention, suitable examples of X-containing starting materials include $X_2O_5$ such as $As_2O_5$, $P_2O_5$, $Sb_2O_5$ or $Bi_2O_5$; $X_2O_3$ such as $As_2O_3$, $Sb_2O_3$ or $Bi_2O_3$, $H_3PO_4$, $H_3PO_3$, $H_2SeO_3$, $H_2SeO_4$, $H_2TeO_3$, $H_2TeO_4$, $H_2SO_4$, $H_4SiO_4$, $Na_4SiO_4$, $AlCl_3$, $GaCl_3$ and $GeCl_4$. In an especially preferred embodiment, the noble metal M source, preferably $Pd(CH_3COO)_2$, is reacted with $As_2O_5$.

If the resulting POM is to contain one or more groups R, the X-containing starting material also contains R. In particular, an X-containing starting material is used in which R is covalently bound to X. For example, R-containing derivatives of phosphonic acid, arsonic acid, trichlorosilane and trichlorogermanium can be used. In a preferred embodiment of the present invention examples of suitable XR-containing starting materials include methylphosphonic acid, phosphonoacetic acid, 2-carboxyethylphosphonic acid, phenylphosphonic acid, methylarsonic acid, ethylarsonic acid, propylarsonic acid, butylarsonic acid, p-arsanilic acid, DL-2-amino-4-arsonobutanoic acid monohydrate, p-aminophenylarsonic acid, ammonium 4-nitrophenylarsonate, ammonium-4-hydroxyphenyl-arsonic acid chloride dihydrate, 3-nitro-4-hydroxyphenylarsonic acid, 4-hydroxyphenylarsonic acid, methyltrichlorosilane, ethyltrichlorosilane, β-chloroethyl-trichlorosilane, phenyltrichlorosilane, methylgermanium trichloride, ethylgermanium trichloride, phenylgermanium trichloride and methylgermanium triiodide. In order to link a POM oxo-cluster with at least one other POM oxo-cluster, R can be substituted with at least one further X-containing moiety. In another preferred embodiment of the present invention, examples of X-R-X-containing starting materials which can be used in step (a) of the one-pot process and in step (a) of the two-pot process include methylenediphosphonic acid, 1,2-ethylenediphosphonic acid, 2-hydroxypropane-1,3-bis(arsonic acid), 1R(S),2S(R)-1,2-bis(trichlorosilyl)-1,2-diphenyl ethane, 1,3-bis(trichlorosilylmethyl)benzene, 1,4-bis(trichlorosilylmethyl)benzene and 1,1,1,4,4,4-hexachloro-1,4-disilabutane. In another preferred embodiment of the present invention suitable examples of X-containing starting materials which comprise more than two X moieties include nitrilotris (methylphosphonic acid) and hexakis(3-(trichlorosilyl)propyl)benzene. Most preferably, the X-containing starting material which also contains one or more R is water-soluble.

In a preferred embodiment, step (a) of the one-pot process and step (a1) of the two-pot process are carried out in an aqueous solution. If the X-containing starting material has only a low solubility in water (for example, because it also contains one or more groups R) it is possible to dissolve the X-containing starting material in a small volume of organic solvent and then adding this solution to an aqueous solution of the sources of M and M" or vice versa. Examples of suitable organic solvents include, but are not limited to acetonitrile, acetone, toluene, DMF, DMSO, ethanol, methanol, n-butanol, sec-butanol, isobutanol and mixtures thereof. It is also possible to use emulsifying agents to allow the reagents of step (a) of the one-pot process and step (a1) of the two-pot process to undergo a reaction.

Furthermore, in a preferred embodiment of the present invention, in step (a) of the one-pot process, the concentration of the noble metal ions originating from the at least one source of M ranges from 0.005 to 5 mole/l, preferably from 0.01 to 1 mole/l, more preferably from 0.01 to 0.1 mole/l, the concentration of the metal ions originating from the at least one source of M' ranges from 0.0005 to 0.5 mole/l, preferably 0.001 to 0.1 mole/l, more preferably 0.005 to 0.05 mole/l, the concentration of the noble metal ions originating from the at least one source of M" ranges from 0.0005 to 0.5 mole/l, preferably 0.001 to 0.1 mole/l, more preferably 0.005 to 0.05 mole/l, and the concentration of the at least one X-containing starting material ranges from 0.0005 to 5 mole/l, preferably 0.001 to 1 mole/l, more preferably 0.005 to 0.1 mole/l, with the proviso that the ratio of the molar concentration of the metal ions originating from the at least one source of M to the molar concentration of the metal ions originating from the at least one source of M' is in the range from 0.1 to 50, preferably from 1 to 20, more preferably from 1 to 10.

In a preferred embodiment of the present invention, in step (a1) of the two-pot process, the concentration of the noble metal ions originating from the at least one source of M ranges from 0.005 to 5 mole/l, preferably from 0.01 to 1 mole/l, more preferably from 0.01 to 0.1 mole/l, the concentration of the noble metal ions originating from the at least one source of M" ranges from 0.0005 to 0.5 mole/l, preferably 0.001 to 0.1 mole/l, more preferably 0.005 to 0.05 mole/l, and the concentration of the at least one X-containing starting material ranges from 0.0005 to 5 mole/l, preferably 0.001 to 1 mole/l, preferably 0.005 to 0.1 mole/l.

Furthermore, in a preferred embodiment, the pH of the aqueous solution in step (a) of the one-pot process and step (a1) of the two-pot process ranges from 2 to 14, preferably from 4 to 10 and more preferably from 6 to 8. Most preferably, the pH is about 6.5 to 7.5. Generally, in a preferred embodiment of the present invention a buffer solution can be used for maintaining the pH value in a certain range. It is particularly preferred to use a sodium acetate buffer having a concentration of 0.5 M (or 0.5 mole/l) and a pH of about 6.5 to 8.5, preferably a pH of about 7.5, as aqueous solvent. In another embodiment, the concentration of the aqueous buffer solution (preferably sodium acetate buffer solution) is from 0.05 to 1.5 M, preferably 0.1 to 1.0 M, more preferably from 0.25 to 0.75 M, most preferably about 0.5 M. Generally, in a preferred embodiment of the present invention additional base solution can be used for adjusting the pH to a certain pH value. It is particularly preferred to use aqueous sodium hydroxide solution having a concentration of 6 M. In another embodiment, the concentration of the aqueous base solution (preferably aqueous sodium hydroxide solution) is from 0.1 to 12 M, preferably 1 to 10 M, preferably from 3 to 8 M, preferably about 6 M.

A very preferred embodiment of the present invention is the one-pot process, wherein in step (a) the at least one source of M, the at least one source of M', the at least one source of M", the at least one source of X-containing and optionally the at least one source of R-containing starting material are dissolved in a solution of sodium acetate buffer, preferably an 0.1 to 1.0 M solution of sodium acetate buffer, in particular a 0.25 to 0.75 M solution of sodium acetate buffer, and most preferred a 0.5 M solution of sodium acetate buffer.

A very preferred embodiment of the present invention is the two-pot process, wherein in step (a1) the at least one source of M, the at least one source of M", the at least one source of X-containing and optionally the at least one source of R-containing starting material are dissolved in a solution of sodium acetate buffer, preferably an 0.1 to 1.0 M solution of sodium acetate buffer, in particular a 0.25 to 0.75 M solution of sodium acetate buffer, and most preferred a 0.5 M solution of sodium acetate buffer.

In step (a) of the one-pot process or the two-pot process of the present invention, the reaction mixture is typically heated to a temperature of from 20° C. to 100° C., preferably from 50° C. to 90° C., preferably from 70° C. to 80° C., preferably from 75° C. to 80° C., and most preferably about 80° C.

In step (a) of the one-pot process or the two-pot process of the present invention, the reaction mixture is typically heated for about 10 min to about 4 h, more preferably for about 30 min to 2 h, most preferably for about 100 min. Further, it is preferred that the reaction mixture is stirred during step (a).

With regard to step (a) of the two pot process of the present invention the term reaction mixture refers to the mixture of reaction steps (a1) and (a3) exclusively, but not to the mixture of isolating step (a2) which is referred to as crude mixture. With regard to the present invention the term crude mixture relates to an unpurified mixture after a reaction step and is thereby used synonymously with reaction mixture of the preceding reaction step.

In a preferred embodiment of the two-pot process of the present invention, the crude mixture is filtered between step (a1) and (a2). Preferably, the crude mixture is filtered immediately after the end of step (a1), i.e. immediately after the stirring is turned off, and is then optionally cooled. Alternatively, if applicable, the crude mixture is cooled first, preferably to room temperature, and subsequently filtered. The purpose of this filtration is to remove solid impurities after step (a1). Thus, the product of step (a1) remains in the filtrate.

In step (a2) of the two-pot process the product of step (a1) is isolated from the reaction mixture of step (a1) or from the corresponding filtrate. For example, isolation of the product of step (a1) can be effected by common techniques including bulk precipitation or crystallization. In a preferred embodiment of the present invention the product of step (a1) is isolated as crystalline or amorphous solid, preferably as crystalline solid. Crystallization or precipitation can be effected by common techniques such as evaporation or partial evaporation of the solvent, cooling, change of solvent, solvents or solvent mixtures, addition of crystallization seeds, etc. In a preferred embodiment the addition of any suitable cation species can induce crystallization or precipitation of the desired salt of the product of step (a1), wherein fractional crystallization is preferable. In a preferred embodiment, fractional crystallization might be accomplished by the slow addition of a specific amount of any suitable cation to the reaction mixture of step (a1) of the two-pot process or to its corresponding filtrate.

Optional purification in step (a2) of the two-pot process can be accomplished by re-crystallization or re-dissolution and re-precipitation. In a preferred embodiment the isolated product of step (a2) of the two-pot process is dissolved in a suitable solvent or solvent mixture, preferably water or an aqueous mixture. In a preferred embodiment of the present invention, the purified product of step (a2) is isolated as crystalline or amorphous solid, preferably as crystalline solid. Crystallization or precipitation can be effected by common techniques such as evaporation or partial evaporation of the solvent, cooling, change of solvent, solvents or solvent mixtures, addition of crystallization seeds, etc. In a preferred embodiment the addition of any suitable cation species can induce crystallization or precipitation of the desired salt of the purified product in step (a2), wherein fractional crystallization is preferable. In a preferred embodiment, fractional crystallization might be accomplished by the slow addition of a specific amount of any suitable cation to the mixture in optional purification step (a2) of the two-pot process which might be beneficial for product purity and yield.

With regard to the present invention the any suitable cation in step (a2) of the two-pot process can be any cation capable of inducing crystallization of a species comprising the desired anionic product. In one embodiment the any suitable cation is a cation "A". In another embodiment the any suitable cation is different from cation "A".

In a preferred embodiment, step (a3) of the two-pot process is carried out in an aqueous solution. If any of the substrates, including the product of step (a2) and the at least one source of M', or reagents has only a low solubility in water it is possible to add small volumes of organic solvent or aqueous organic solvent to the, preferably aqueous, reaction mixture or vice versa. Examples of suitable organic solvents include, but are not limited to acetonitrile, acetone, toluene, DMF, DMSO, ethanol, methanol, n-butanol, sec-butanol, isobutanol and mixtures thereof. It is also possible to use emulsifying agents to allow the substrates and reagents of step (a3) of the two-pot process to undergo a reaction.

Furthermore, in a preferred embodiment of the present invention in step (a3) of the two-pot process the concentration of the product of step (a2) ranges from 0.0001 to 1 mole/l, preferably from 0.0005 to 0.5 mole/l, more preferably from 0.001 to 0.1 mole/l and the concentration of the metal ions originating from the at least one source of M' ranges from 0.0005 to 0.5 mole/l, preferably 0.001 to 0.1 mole/l, more preferably 0.005 to 0.05 mole/l.

In a preferred embodiment, the pH of the aqueous solution in step (a3) of the two-pot process ranges from 2 to 14, preferably from 4 to 10 and more preferably from 6 to 8. Most preferably, the pH is about 6.5 to 7.5. Generally, in a preferred embodiment of the present invention, a buffer solution can be used for maintaining the pH value in a certain range. It is particularly preferred to use a sodium acetate buffer having a concentration of 0.5 M and a pH of about 6.5 to 8.5, preferably a pH of about 7.5, as aqueous solvent. In another embodiment, the concentration of the aqueous buffer solution (preferably sodium acetate buffer solution) is from 0.05 to 1.5 M, preferably 0.1 to 1.0 M, more preferably from 0.25 to 0.75 M, most preferably about 0.5 M. Generally, in a preferred embodiment of the present invention, additional base solution or acid solution can be used for adjusting the pH to a certain pH value. It is particularly preferred to use aqueous sodium hydroxide or $H_2SO_4$ solution having a concentration of 6 M. In another embodiment, the concentration of the aqueous base or acid solution (preferably aqueous sodium hydroxide or $H_2SO_4$ solution) is from 0.1 to 12 M, preferably 1 to 10 M, preferably from 3 to 8 M, preferably about 6 M.

In the context of the present invention the pH of the aqueous solution in step (a) of the one-pot process and steps (a1) and (a3) of the two-pot process refers to the pH as measured at the end of the reaction. In the preferred embodiment where e.g. an aqueous sodium hydroxide solution is used for adjusting the pH-value, the pH is measured after the adjustment at the end of the reaction. pH values are at 20° C., and are determined to an accuracy of ±0.05 in accordance with the IUPAC Recommendations 2002 (R. P. Buck et al., Pure Appl. Chem., Vol. 74, No. 11, pp. 2169-2200, 2002).

A suitable and commercially available instrument for pH measurement is the Mettler Toledo FE20 pH meter. The pH calibration is carried out as 2-point calibration using a pH=4.01 standard buffer solution and a pH=7.00 standard buffer solution. The resolutions are: 0.01 pH; 1 mV; and 0.1° C. The limits of error are: ±0.01 pH; ±1 mV; and ±0.5° C.

A very preferred embodiment of the present invention is the two-pot process, wherein in step (a3) the product of step (a2) and the at least one source of M' are dissolved in a solution of sodium acetate buffer, preferably an 0.1 to 1.0 M solution of sodium acetate buffer, in particular a 0.25 to 0.75 M solution of sodium acetate buffer, and most preferred a 0.5 M solution of sodium acetate buffer.

In step (a3) of the two-pot process of the present invention, the reaction mixture is typically heated to a temperature of from 20° C. to 100° C., preferably from 50° C. to 90° C., preferably from 70° C. to 80° C. preferably from 75° C. to 80° C., and most preferably about 80° C.

In step (a3) of the two-pot process of the present invention, the reaction mixture is typically heated for about 10 min to about 4 h, more preferably for about 30 min to 2 h, most preferably for about 100 min. Further, it is preferred that the reaction mixture is stirred during step (a3).

In a preferred embodiment of the one-pot process or the two-pot process, between steps (a) and (b), the crude mixture is filtered. Preferably, the crude mixture is filtered immediately after the end of step (a), i.e. immediately after the stirring is turned off, and is then optionally cooled. Alternatively, if applicable the heated crude mixture is cooled first, preferably to room temperature, and subsequently filtered. The purpose of this filtration is to remove solid impurities after step (a). Thus, the product of step (a) remains in the filtrate.

In a preferred embodiment, in case cation A is not present in the crude mixture or filtrate already, or the concentration of A in the crude mixture or filtrate should be increased, in step (b) of the one-pot or two-pot process, a salt of the cation A can be added to the reaction mixture of step (a) of the one-pot or two-pot process or to its corresponding filtrates to form $(A_n)^{m+}\{M'_s[M''M_{12}X_8O_yR_zH_q]\}^{m-}$. Preferably, the salt of A is added as a solid or in the form of an aqueous solution. The counterions of A can be selected from the group consisting of any stable, non-reducing, water-soluble anion, e.g., halides, nitrate, sulfate, acetate, phosphate. Preferably, the acetate or phosphate salt is used. However, the addition of extra cations A in step (b) of the one-pot or two-pot process is not necessary if the desired cations are already present during step (a) of the one-pot or two-pot process, for example, as a component of the buffer preferably used as solvent in step (a) of the one-pot process or steps (a1) or (a3) of the two-pot process or a component of any of the sources of X, M, M' and/or M" including, for example, palladium and platinum cations themselves or a component used in the isolation step (a2) of the two-pot process. Preferably, all desired cations are already present during step (a) of the one-pot or two-pot process, thus, that there is no optional addition of extra cations necessary.

In step (c) of the one-pot or two-pot process, the POMs according to the invention or solvate thereof, formed in step (a) or (b) of the one-pot process or step (a3) or (b) of the two-pot process, are recovered. For example, isolation of the POMs or solvate thereof can be effected by common techniques including bulk precipitation or crystallization. In a preferred embodiment of the present invention the POMs are isolated as crystalline or amorphous solids, preferably as crystalline solids. Crystallization or precipitation can be effected by common techniques such as evaporation or partial evaporation of the solvent, cooling, change of solvent, solvents or solvent mixtures, addition of crystallization seeds, etc. In a preferred embodiment the addition of cation A in step (b) of the one-pot or two-pot process can induce crystallization or precipitation of the desired POM $(A_n)^{m+}\{M'_s[M''M_{12}X_8O_yR_zH_q]\}^{m-}$, wherein fractional crystallization is preferable. In a preferred embodiment, fractional crystallization might be accomplished by the slow addition of a specific amount of cation A to the reaction mixture of step (a) of the one-pot process or step (a1) of the two-pot process or to its corresponding filtrates which might be beneficial for product purity and yield.

A preferred embodiment of the present invention is a process according to the one-pot process or the two-pot process, wherein water is used as solvent, the at least one source of M is a water-soluble salt of $Pt^{II}$ or $Pd^{II}$, preferably selected from platinum chloride, palladium nitrate, palladium sulfate, palladium chloride or palladium acetate, in particular a salt of $Pd^{II}$ selected from palladium nitrate, palladium sulfate, palladium chloride or palladium acetate, such as palladium chloride or palladium acetate; the at least one source of M' is a water-soluble gold or silver salt, preferably selected from gold chloride, gold hydroxide, silver nitrate, silver fluoride or silver chloride, in particular a silver salt such as silver nitrate; the at least one source of M" is a water-soluble salt of M", for instance palladium acetate, palladium chloride, palladium nitrate and/or palladium sulfate when M" is $Pd^{II}$; and the at least one source of X is an oxide of X such as $As_2O_5$, $P_2O_5$, $Sb_2O_5$, $Bi_2O_5$, $As_2O_3$, $Sb_2O_3$, or $Bi_2O_3$, preferably $As_2O_5$.

A very preferred embodiment of the present invention is a process according to the one-pot process or the two-pot process, wherein water is used as solvent, the at least one source of M is a water-soluble salt of $Pd^{II}$, preferably palladium nitrate, palladium sulfate, palladium chloride or palladium acetate, the at least one source of M' is a water-soluble silver salt, preferably silver nitrate, the at least one source of M" is a water-soluble salt of M", for instance palladium acetate, palladium chloride, palladium nitrate and/or palladium sulfate when M" is $Pd^{II}$, and the at least one source of X is an oxide of X, preferably $As_2O_5$.

A most preferred embodiment of the present invention is a process according to the one-pot process or the two-pot process, wherein water is used as solvent, the at least one source of M is a water-soluble salt of $Pd^{II}$, preferably palladium nitrate, palladium sulfate, palladium chloride or palladium acetate, the at least one source of M' is a water-soluble silver salt, preferably silver nitrate, the at least one source of M" is a water-soluble salt of M", for instance palladium acetate, palladium chloride, palladium nitrate and/or palladium sulfate when M" is $Pd^{II}$, the at least one source of M" is the same as or different from the source of M, preferably the same, and the at least one source of X is an oxide of X, preferably $As_2O_5$.

According to one embodiment, the present POMs can be immobilized on a solid support. The present invention thus also relates to supported POMs comprising the POMs of the present invention or prepared by the process of the present invention on a solid support. Suitable supports include but are not limited to materials having a high surface area and/or a pore size which is sufficient to allow the POMs to be loaded, e.g., polymers, graphite, carbon nanotubes, electrode surfaces, aluminium oxide and aerogels of aluminum oxide and magnesium oxide, titanium oxide, zirconium oxide, cerium oxide, silicon dioxide, silicates, active carbon, mesoporous materials, like mesoporous silica, such as SBA-15 and MCM-41, zeolites, aluminophosphates (ALPOs), silicoaluminophosphates (SAPOs), metal organic frameworks (MOFs), zeolitic imidazolate frameworkds (ZIFs), periodic mesoporous organosilicas (PMOs), and mixtures thereof and modified compounds thereof. Preferred supports are, for instance, mesoporous silica, more preferably SBA-15 or MCM-41, most preferably SBA-15. A variety of such solid supports is commercially available or can be prepared by common techniques. Furthermore, there are various common techniques to modify or functionalize solid supports, for example with regard to the size and shape of the surface or the atoms or groups available for bonding on the surface.

In a preferred embodiment of the present invention the immobilization of the POMs to the surface of the solid support is accomplished by means of adsorption, including physisorption and chemisorption, preferably physisorption. The adsorption is based on interactions between the POMs and the surface of the solid support such as van-der-Waals interactions, hydrogen-bonding interactions, ionic interactions, etc.

In a preferred embodiment the negatively charged oxo-clusters $\{M'_s[M''M_{12}X_8O_yR_zH_q]\}$ are adsorbed predominantly based on ionic interactions. Therefore, a solid support bearing positively charged groups is preferably used, in particular a solid support bearing groups that can be positively charged by protonation. A variety of such solid supports is commercially available or can be prepared by common techniques. In one embodiment the solid support is functionalized with positively charged groups, preferably groups that are positively charged by protonation, and the negatively charged oxo-cluster $\{M'_s[M''M_{12}X_8O_yR_zH_q]\}$ is linked to said positively charged groups by ionic interactions. In a preferred embodiment the solid support, preferably mesoporous silica, more preferably SBA-15 or MCM-41, most preferably SBA-15, is functionalized with moieties bearing positively charged groups, preferably tetra-hydrocarbyl ammonium groups, more preferably groups that can be positively charged by protonation, most preferably mono-functionalized amino groups —$NH_2$. Preferably said groups are attached to the surface of the solid support by covalent bonds, preferably via a linker that comprises one or more, preferably one, of said groups, preferably an alkyl, aryl, alkenyl, alkynyl, hetero-alkyl, hetero-cycloalkyl, hetero-alkenyl, hetero-cycloalkenyl, hetero-alkynyl, hetero-aryl or cycloalkyl linker, more preferably an alkyl, aryl, hetero-alkyl or hetero-aryl linker, more preferably an alkyl linker, most preferably a methyl, ethyl, n-propyl, n-butyl, n-pentyl, n-hexyl linker, in particular a n-propyl linker. Preferably said linkers are bonded to any suitable functional group present on the surface of the solid support, such as to hydroxyl groups. Preferably said linkers are bonded to said functional groups present on the surface of the solid support either directly or via another group or atom, most preferably via another group or atom, preferably a silicon-based group, most preferably a silicon atom. In a most preferred embodiment of the present invention the POMs are supported on (3-aminopropyl)triethoxysilane (apts)-modified SBA-15.

In the supported POMs of the present invention, the POMs that are immobilized on the solid support are in the form of primary and/or secondary particles. In an especially preferred embodiment, the immobilized POMs particles are mainly in the form of primary particles (i.e. non-agglomerated primary particles), that is at least 90 wt % of the immobilized POMs particles are in the form of primary particles, preferably at least 95 wt %, more preferably at least 99 wt %, in particular substantially all the immobilized POMs particles are in the form of primary particles.

The invention is further directed to processes for preparing supported POMs according to the invention. Solid supports used in the context of this invention are as defined above. In a preferred embodiment of the present invention the surface of the solid supports is modified with positively charged groups, more preferably groups that can be positively charged by protonation. Those charged solid supports can be prepared by techniques well established in the art, for example by the surface modification of a mesoporous silica, such as SBA-15, with a suitable reagent bearing a positively charged group or a group that can be positively charged by protonation, such as 3-aminopropyltriethoxysilane (apts), is conducted by heating, preferably under reflux, under inert gas atmosphere, such as argon or nitrogen, in an inert solvent with a suitable boiling point, such as hexane, heptane or toluene, for a suitable time, such as 4-8 hours, and finally the modified solid support is isolated, preferably by filtration, purified, preferably by washing, and dried, preferably under vacuum by heating, most preferably under vacuum by heating at about 100° C.

The optionally treated support may be further calcined at a temperature of 500° C. to 800° C. For the calcination, common equipment may be used, that is commercially available. Calcination of the optionally treated support may for instance be conducted under an oxygen containing gas such as air, under vacuum, under hydrogen or under an inert gas such as argon or nitrogen, more preferably under inert gas, most preferably under nitrogen.

The POMs according to the present invention or prepared by the process of the present invention can be immobilized on the surface of the solid support by contacting said POMs with the solid support. The present invention therefore also relates to a process for the preparation of supported POMs, comprising the step of contacting the POMs provided by the present invention or prepared according to the present invention with the solid support, thereby immobilizing at least part of the POMs onto the support; and optionally isolating the resulting supported POMs.

Said contacting may be conducted employing common techniques in the art, such as blending both the solid support and the POM in the solid form. In a preferred embodiment the POM is mixed with a suitable solvent, preferably water or an aqueous solvent, and the solid support is added to this mixture. In a more preferred embodiment the solid support is mixed with a suitable solvent, preferably water or an aqueous solvent, and the POM is added to this mixture. In case a solid support with groups that can be positively charged by protonation is used, the mixture is preferably acidified, for instance by addition of $H_2SO_4$, $HNO_3$ or $HCl$, most preferably by addition of $H_2SO_4$ or $HNO_3$, so that the pH value of the mixture ranges from 0.1 to 6, preferably from 1 to 4 and more preferably from 1.5 to 3, most preferably is a pH of about 2. The mixture comprising POM, solid support and solvent is preferably stirred, typically for 1 min to 24 h, more preferably for 30 min to 15 h, more preferably for 1 h to 12 h, most preferably for 6 h to 10 h, in particular about 8 h. While stirring, preferably the mixture is heated to a temperature of from 20° C. to 100° C., preferably from 20° C. to 80° C., preferably from 20° C. to 60° C. preferably from 20° C. to 40° C., and most preferably about 25° C. Afterwards, the supported POM can be kept in the solvent as suspension or can be isolated. Isolation of the supported POM from the solvent may be performed by any suitable method in the art, such as by filtration, evaporation of the solvent, centrifugation or decantation, preferably by filtration or removal of the solvent in vacuum, more preferably by filtration. The isolated supported POMs may then be washed with a suitable solvent, preferably water or an aqueous solvent, and dried. Supported POMs may be dried in an oven at a temperature of e.g. about 100° C.

In another embodiment, the supported POMs may be further calcined at a temperature not exceeding the transformation temperature of the POM, i.e. the temperature at which decomposition of the POM starts to take place (usually about 600-700° C. for the present POMs according to their corresponding TGA). Thus, in a preferred embodiment the POMs of the present invention are thermally stable up to temperatures of around 600-700° C. For the calcination, common equipment may be used, that is commercially available. Calcination of the supported POMs may for instance be conducted under an oxygen containing gas such as air, under vacuum, under hydrogen or under an inert gas such as argon or nitrogen, more preferably under inert gas, most preferably under nitrogen.

In many cases, however, and in particular if the supported POM is used as a catalyst or pre-catalyst under reductive conditions, drying of the supported POM without calcination may be sufficient.

In supported POMs, the POM loading levels on the solid support may be up to 30 wt. % or even more but are preferably up to 10 wt %, for instance up to 5 wt % or even up to 2 wt %. Accordingly, the POM loading level on the solid support is typically of 0.01 to 30 wt. %, particularly 0.05 to 20 wt. %, more particularly 0.1 to 10 wt. %, often 0.2-6 wt. %, more often 0.3-5 wt. %, and most often 0.5-2 wt. %. POM loading levels on the solid support can be determined by elemental analysis such as Inductively Coupled Plasma Mass Spectrometry (ICP-MS) analysis, for instance using a Varian Vista MPX.

According to one embodiment, the present invention also relates to metal-clusters of the formula $$\{M^o{}_s[M''M^o{}_{12}]\}$$

wherein all $M^o$ are the same, and are selected from the group consisting of $Pd^o$, $Pt^o$, $Rh^o$, $Ir^o$, $Ag^o$, and $Au^o$, preferably $Pd^o$, $Pt^o$, $Rh^o$, $Ir^o$, and $Au^o$, more preferably $Pd^o$, $Pt^o$ and $Rh^o$, most preferably $Pd^o$ and $Pt^o$, in particular $Pd^o$, each $M'^o$ is independently selected from the group consisting of $Rh^o$, $Ir^o$, $Pd^o$, $Pt^o$, $Ag^o$, $Au^o$, $Cd^o$, $Hg^o$ and mixtures thereof, preferably $Rh^o$, $Ir^o$, $Pd^o$, $Pt^o$, $Ag^o$, $Au^o$ and mixtures thereof, more preferably $Pd^o$, $Pt^o$, $Ag^o$, $Au^o$ and mixtures thereof, most preferably $Ag^o$, $Au^o$ and mixtures thereof, in particular $Ag^o$, s is a number from 1 to 8, preferably 2 to 6, more preferably 2 to 4, most preferably 2 or 4, in particular 4, and M'' is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg and lanthanide metal, preferably Sr, Sc, Ti, V, Cr, Mn, Fe, Co, Ni, Cu, Zn, Y, Zr, Ru, Rh, Pd, Ag, Cd, Lu, Re, Os, Ir, Pt and Au, more preferably Ti, V, Cr, Mn, Fe, Co, Ni, Cu, Zn, Ru, Rh, Pd, Ag, Re, Os, Ir, Pt and Au, most preferably Rh, Pd, Ag, Ir, Pt and Au, in particular Pd and the oxidation state of M'' is 0 or greater than 0, preferably 0 to V, more preferably 0 to IV, most preferably 0 to III, in particular 0.

The above definition of the metal-cluster $\{M^o{}_s[M''M^o{}_{12}]\}$ allows all of $M^o$, $M'^o$ and M'' to be the same metal. However, this is not preferred.

Preferably the metal-cluster $\{M^o{}_s[M''M^o{}_{12}]\}$ comprises at least two different metals. There are e.g. the following alternative possibilities for metal-clusters comprising at least two different metals:

(a) $M^o \neq M'^o$ and $M^o \neq M''$ and $M'^o \neq M''$
(b) $M^o = M'^o$ and $M^o \neq M''$ and $M'^o \neq M''$
(c) $M^o \neq M'^o$ and $M^o = M''$ and $M'^o \neq M''$
(d) $M^o \neq M'^o$ and $M^o \neq M''$ and $M'^o = M''$ The $M'^o{}_s$ are independently selected and hence may be different among each other.

$M^o = M'^o$ means that all $M'^o$ are the same among each other and are the same as $M^o$. $M'^o = M''$ means that all $M'^o$ are the same among each other and are the same metal as M'', but the oxidation state of M'' may be different from that of $M'^o$. $M^o = M''$ means that $M^o$ is the same metal as M'', but the oxidation state of M'' may be different from that of $M^o$.

$M^o \neq M'^o$ either means that all $M'^o$ are the same among each other, and hence all $M'^o$ are different from $M^o$; or that the $M'^o$ are different among each other, but still all $M'^o$ are different from $M^o$; or that the $M'^o$ are different among each other, and only some of the $M'^o$ are different from $M^o$. The latter alternative is less preferred.

$M'^o \neq M''$ either means that all $M'^o$ are the same among each other, and hence all $M'^o$ are different from $M''$; or that the $M'^o$ are different among each other, but still all $M'^o$ are different from $M''$; or that the $M'^o$ are different among each other, and only some of the $M'^o$ are different from $M''$. The latter alternative is less preferred.

Thus, alternative (c) above encompasses the less preferred embodiment wherein $M^o$ and $M''$ are the same metal and are the same as some of the $M'^o$ while the remainder of the $M'^o$ are different.

Alternatives (a), (c) and (d) are preferred, with the proviso that all $M'^o$ are different from $M^o$. Thus, metal-clusters are preferred wherein all $M'^o$ are different from $M^o$. Particularly preferred are metal clusters wherein all $M'^o$ are the same and all $M'^o$ are different from $M^o$. Alternative (c) is the most preferred, wherein all $M^o$ and $M''$ are the same and all $M^o$ and $M''$ are different from $M'^o$.

The above considerations apply mutatis mutandis also to the formula $(A_n)^{m+}\{M'_s[M''M_{12}X_8O_yR_zH_q]\}^{m-}$ of the POM.

In an especially preferred embodiment, the invention relates to metal-clusters represented by the formula $\{Ag_4[Pd_{13}]\}$ or $\{Ag_2[Pd_{13}]\}$.

Further, suitable examples of metal-clusters according to the invention are represented by the formulae $\{M'^o_8[M''M^o_{12}]\}$, e.g., $\{M'^o_4[M''M^o_{12}]\}$, $\{M'^o_8[M''Pd^o_{12}]\}$, such as $\{M=^o_4[M''Pd^o_{12}]\}$, $\{Ag^o_4[M''Pd^o_{12}]\}$, $\{Ag^o_4[PtPd^o_{12}]\}$, $\{Ag^o_4[AuPd^o_{12}]\}$, $\{Au^o_4[AuPd^o_{12}]\}$, $\{Pt^o_4[AgPd^o_{12}]\}$, or $\{M'^o_2[M''M^o_{12}]\}$, such as $\{M'^o_2[M''Pd^o_{12}]\}$, $\{Ag^o_2[M''Pd^o_{12}]\}$, $\{Ag^o_2[PtPd^o_{12}]\}$, $\{Ag^o_2[AuPd^o_{12}]\}$, $\{Au^o_2[AuPd^o_{12}]\}$, $\{Pt^o_2[AgPd^o_{12}]\}$, or $\{M'^o_6[M''M^o_{12}]\}$, such as $\{M'^o_6[M''Pd^o_{12}]\}$, $\{Ag^o_6[M''Pd^o_{12}]\}$, $\{Ag^o_6[Pd^o_{13}]\}$, $\{Ag^o_6[PtPd^o_{12}]\}$, $\{Ag^o_6[AuPd^o_{12}]\}$, $\{Au^o_6[AuPd^o_{12}]\}$, $\{Pt^o_6[AgPd^o_{12}]\}$, or $\{M'^o_8[M''M^o_{12}]\}$, such as $\{M'^o_8[M''Pd^o_{12}]\}$, $\{M'^o_8[M''Pt^o_{12}]\}$, $\{M'^o_8[M''Au^o_{12}]\}$, $\{Au^o_8[CrAg^o_{12}]\}$, $\{Pt^o_8[NiIr^o_{12}]\}$, $\{Ag^o_8[ZnRh^o_{12}]\}$, $\{Pd^o_8[RhPt^o_{12}]\}$, $\{Rh^o_8[IrAu^o_{12}]\}$, $\{Ir^o_8[ReAg^o_{12}]\}$, $\{Pt^o_8[OsIr^o_{12}]\}$, $\{Pd^o_8[ZrRh^o_{12}]\}$, $\{Ag^o_8[HgPt^o_{12}]\}$, $\{Ag^o_8[RuAu^o_{12}]\}$, $\{Au^o_8[VAg^o_{12}]\}$, $\{Au^o_8[PtIr^o_{12}]\}$, and $\{Cd^o_8[RuRh^o_{12}]\}$.

The metal-clusters of the present invention are in the form of primary and/or secondary particles. In an especially preferred embodiment, the metal-clusters provided by the present invention are mainly in the form of primary particles (i.e. non-agglomerated primary particles), that is at least 90 wt % of the metal-clusters are in the form of primary particles, preferably at least 95 wt %, more preferably at least 99 wt %, in particular substantially all the metal-clusters are in the form of primary particles. This includes metal-clusters dispersed in liquid carrier media. The metal-clusters of the present invention preferably have a primary particle size of about 1.0-2.0 nm, for instance about 1.56 nm.

In a further embodiment, the metal-clusters are dispersed in a liquid carrier medium, thereby forming a dispersion of metal-clusters. In one embodiment of the present invention the liquid carrier medium is an organic solvent, optionally combined with one or more dispersing agents. The organic solvent is preferably capable of dissolving the POMs used as starting material for the preparation of the metal-clusters, for instance liquid n-alkanes, e.g., hexane or heptane.

The dispersing agent (or surfactant) is added to the liquid carrier medium to prevent agglomeration of the primary particles of metal-cluster. Preferably, the dispersing agent is present during formation of the primary particles of metal-cluster. An example of a surfactant useful as dispersing agent is citric acid or citrate. The dispersing agent preferably forms micelles, each micelle containing one primary particle of metal-cluster thereby separating the primary particles from each other and preventing agglomeration thereof.

In another further embodiment, the metal-clusters can be immobilized on a solid support thereby forming supported metal-clusters. Suitable supports include but are not limited to materials having a high surface area and/or a pore size which is sufficient to allow the metal-clusters to be loaded, e.g. polymers, graphite, carbon nanotubes, electrode surfaces, aluminium oxide and aerogels of aluminum oxide and magnesium oxide, titanium oxide, zirconium oxide, cerium oxide, silicon dioxide, silicates, active carbon, mesoporous materials, like mesoporous silica, such as SBA-15 and MCM-41, zeolites, aluminophosphates (ALPOs), silicoaluminophosphates (SAPOs), metal organic frameworks (MOFs), zeolitic imidazolate frameworkds (ZIFs), periodic mesoporous organosilicas (PMOs), and mixtures thereof and modified compounds thereof. Preferred supports are, for instance, mesoporous silica, more preferably SBA-15 or MCM-41, most preferably SBA-15.

A variety of such solid supports is commercially available or can be prepared by common techniques. Furthermore, there are various common techniques to modify or functionalize solid supports, for example with regard to the size and shape of the surface or the atoms or groups available for bonding on the surface. In a preferred embodiment of the present invention the immobilization of the metal-clusters to the surface of the solid support is accomplished by means of adsorption, including physisorption and chemisorption, preferably physisorption. The adsorption is based on interactions between the metal-clusters and the surface of the solid support, such as van-der-Waals interactions.

In the supported metal-clusters of the present invention, the metal-clusters that are immobilized on the solid support are in the form of primary and/or secondary particles. In an especially preferred embodiment, the immobilized metal-cluster particles are mainly in the form of primary particles (i.e. non-agglomerated primary particles), that is at least 90 wt % of the immobilized metal-cluster particles are in the form of primary particles, preferably at least 95 wt %, more preferably at least 99 wt %, in particular substantially all the immobilized metal-cluster particles are in the form of primary particles.

In the supported metal-clusters of the present invention, the metal-cluster loading levels on the solid support may be up to 30 wt. % or even more but are preferably up to 10 wt. %, for instance up to 5 wt % or even up to 2 wt %. Accordingly, the metal-cluster loading level on the solid support is typically of 0.01 to 30 wt. %, particularly 0.05 to 20 wt. %, more particularly 0.1 to 10 wt. %, often 0.2-6 wt. %, more often 0.3-5 wt. %, and most often 0.5-2 wt. %. Metal-cluster loading levels on the solid support can be determined by elemental analysis such as Inductively Coupled Plasma Mass Spectrometry (ICP-MS) analysis, for instance using a Varian Vista MPX.

The invention is further directed to processes for preparing metal-clusters according to the invention.

Among the preferred processes for preparing any one of the metal-clusters of the present invention is a process for the preparation of a dispersion of said metal-clusters dispersed in liquid carrier media. Said process comprises:
  (a) dissolving any one of the POMs provided by the present invention or prepared according to the present invention in a liquid carrier medium
  (b) optionally providing additive means to prevent agglomeration of the metal-clusters to be prepared, preferably adding compounds capable of preventing agglomeration of metal-clusters to be prepared, more preferably adding surfactants to enable micelle formation, and
  (c) subjecting the dissolved POM to chemical or electrochemical reducing conditions sufficient to at least partially reduce said POM into corresponding metal-clusters.

In a preferred embodiment in step (a), the liquid carrier medium capable of dissolving the POM used for the preparation of the metal-clusters is an organic solvent, such as liquid n-alkanes, e.g., hexane or heptane.

In a preferred embodiment in step (b), classical capping groups such as diverse types of inorganic and organic anions, such as carboxylates, e.g. citrate, may be used to prevent agglomeration of the metal-clusters to be prepared.

In a preferred embodiment in step (c), the chemical reducing conditions comprise the use of a reducing agent selected from organic and inorganic materials which are oxidizable by $Pd^{II}$, $Pt^{II}$, $Rh^{I}$, $Ir^{I}$, $Ag^{I}$ and $Ag^{III}$, and $Au^{I}$ and $Au^{III}$. Such a chemical reduction can for example be effected by using borohydrides, aluminohydrides, hydrazine, CO or hydrogen, preferably hydrogen, more preferably hydrogen at elevated temperature and pressure, preferably by using hydrogen. In the alternative, the POM in step (c) is reduced electrochemically using a common electrochemical cell.

The metal-clusters of the present invention can be immobilized on the surface of a solid support. The present invention therefore also relates to processes for the preparation of supported metal-clusters according to the present invention. A first process for the preparation of supported metal-clusters comprises contacting the dispersion of metal-clusters provided by the present invention or prepared according to the present invention with a solid support, thereby immobilizing at least part of the dispersed metal-clusters onto the support; and optionally isolating the supported metal-clusters.

In a preferred embodiment, the solid support is added to the dispersion of metal-clusters. The resulting mixture is preferably stirred, typically for 1 min to 24 h, more preferably for 30 min to 15 h, more preferably for 1 h to 12 h, most preferably for 6 h to 10 h, in particular about 8 h. While stirring, preferably the mixture is heated to a temperature of from 20° C. to 100° C., preferably from 20° C. to 80° C., preferably from 20° C. to 60° C. preferably from 20° C. to 40° C., and most preferably about 25° C. Afterwards, the supported metal-clusters are preferably isolated. Isolation of the supported metal-clusters from the solvent may be performed by any suitable method in the art, such as by filtration, evaporation of the solvent, centrifugation or decantation, preferably by filtration or removal of the solvent in vacuum, more preferably by filtration. The isolated supported metal-clusters may then be washed with a suitable solvent, preferably water or an aqueous solvent, and dried, for instance by heating under vacuum.

Another suitable process for the preparation of supported metal-clusters according to the present invention comprises: subjecting supported POM provided by the present invention or prepared according to the present invention to chemical or electrochemical reducing conditions sufficient to at least partially reduce said POM into corresponding metal-clusters; and optionally isolating the supported metal-clusters.

In a preferred embodiment, the chemical reducing conditions comprise the use of a reducing agent selected from organic and inorganic materials which are oxidizable by $Pd^{II}$, $Pt^{II}$, $Rh^{I}$, $Ir^{I}$, $Ag^{I}$ and $Ag^{III}$, and $Au^{I}$ and $Au^{III}$. Such a chemical reduction can for example be effected by using borohydrides, aluminohydrides, hydrazine, CO or hydrogen, preferably hydrogen, more preferably hydrogen at elevated temperature and pressure. In the alternative, the POM in is reduced electrochemically using a common electrochemical cell.

The invention is also directed to the use of optionally supported POMs provided by the present invention or prepared according to the present invention and/or optionally supported or dispersed metal-clusters provided by the present invention or prepared according to the present invention, for catalyzing homogeneous and heterogeneous reductive conversion of organic substrates.

In a preferred embodiment, reductive conversion refers to homogeneous or heterogeneous reduction and/or hydroprocessing and/or hydrocracking and/or (hydro)desulfurization of organic substrate.

Within the present reductive conversion of organic substrates, a variety of reducing reagents can be used, including hydrogen or a hydrogen-containing atmosphere.

Since the peripheral M' of the optionally supported POMs of the present invention bear at least partially substitution-labile ligands and since the peripheral M' and the external M metal atoms are not fully sterically shielded by the polyanion backbone, various noble metal coordination sites are easily accessible to the organic substrate and the reducing reagent or reduction active transfer molecule and therefore high catalytic activities are achieved. Further, the remarkable thermal stability of the optionally supported POMs of the present invention permits their use under a great variety of reaction conditions.

Compared with the optionally supported POMs of the present invention, the accessibility of the noble metal atoms in the optionally supported or dispersed metal-clusters of the present invention is even better because of the absence of any ligands. Further, the remarkable thermal stability of the optionally supported or dispersed metal-clusters of the present invention is at least comparable to the one of the optionally supported POMs therefore permitting their use under a great variety of reaction conditions.

It is contemplated that the optionally supported POMs of the present invention can be reduced under the reductive reaction conditions of the reductive conversion described herein. Thus, it might be possible that the optionally supported POMs are reductively converted into metal-cluster-like structures or even into metal-clusters under the conversion reaction conditions and it might be possible that said metal-cluster-like structures or said metal-clusters are actually the catalytically active species. Nevertheless, the optionally supported POMs of the present invention give excellent results in homogeneous and heterogeneous reductive conversion of organic substrates, regardless of the specific nature of the actually catalytically active species. Another useful aspect of this invention is that the optionally supported POMs and/or optionally supported or dispersed metal-clusters of the present invention can be recycled and used multiple times for the reduction of organic molecules.

In a preferred embodiment this invention thus also relates to a process for reducing organic substrates comprising the steps:
  (a) contacting a first organic substrate under addition of hydrogen with one or more optionally supported POMs and/or one or more supported metal-clusters,
  (b) recovering the one or more optionally supported POMs and/or one or more supported metal-clusters;
  (c) contacting the one or more optionally supported POMs and/or one or more supported metal-clusters with a solvent at a temperature of 50° C. or more, and/or hydrogen stripping the one or more optionally supported POMs and/or one or more supported metal-clusters at elevated temperature, and/or calcining the one or more optionally supported POMs and/or one or more supported metal-clusters at elevated temperature under an oxygen containing gas, e.g. air, or under an inert gas, e.g. nitrogen or argon, to obtain a recycled one or more optionally supported POMs and/or one or more supported metal-clusters;
  (d) contacting the recycled one or more optionally supported POMs and/or one or more supported metal-clusters under addition of hydrogen with a second organic substrate which may be the same as or different from the first organic substrate; and
  (e) optionally repeating steps (b) to (d).

The contacting of organic substrate under addition of hydrogen with optionally supported POM and/or supported metal cluster in step (a) may e.g. be carried out in a continuously stirred tank reactor (CSTR), a fixed bed reactor, a fluidized bed reactor or a moving bed reactor.

Thus, e.g., the optionally supported POMs and/or supported metal-clusters of the present invention can be collected after a reduction reaction, washed with a polar or non-polar solvent such as acetone and then dried under heat (typically 50° C. or more, alternately 100° C. or more, alternately 125° C. or more, alternately 150° C. or more) for 30 minutes to 48 hours, typically for 1 to 24 hours, more typically for 2 to 10 hours, more typically for 3 to 5 hours.

Alternatively to or in addition to the washing, the optionally supported POMs and/or supported metal-clusters may be subjected to hydrogen stripping at elevated temperature. Preferably, the hydrogen stripping is carried out at a temperature of 50° C. or higher, more preferably in the range from 200° C. to 500° C. and most preferably from 350° C. to 500° C.

Alternatively to or in addition to the washing and/or hydrogen stripping, the optionally supported POMs and/or supported metal-clusters may be calcined at elevated temperature under an oxygen containing gas, e.g. air, or under an inert gas, e.g. nitrogen or argon. Preferably, the calcination is carried out at a temperature in the range from 600° C. to 700° C.

The washing and/or hydrogen stripping and/or calcining has the effect of regenerating the optionally supported POMs and/or supported metal-clusters for recycling.

The recycled optionally supported POMs and/or supported metal-clusters of the present invention may be used on fresh organic molecules, or on recycled organic molecules from a recycle stream.

It is preferred to use supported POMs and/or supported metal-clusters of the present invention as catalysts with regard to recovery and recycling of the catalyst in the reductive conversion processes described herein. Advantageously, the supported POMs and/or supported metal-clusters of the present invention may be recycled and used again under the same or different reaction conditions. Typically the supported POMs and/or supported metal-clusters are recycled at least 1 time, preferably at least 4 times, preferably at least 8 times, preferably at least 12 times, preferably at least 100 times.

Thus, this invention also relates to a process for reducing organic substrates (typically an arene) which process comprises contacting a first organic substrate with one or more supported POMs and/or supported metal-clusters of the present invention, thereafter recovering the supported POMs and/or supported metal-clusters of the present invention, contacting the supported POMs and/or supported metal-clusters of the present invention with a solvent (such as acetone) at a temperature of 50° C. or more, and/or hydrogen stripping the supported POMs and/or supported metal-clusters at elevated temperature, and/or calcining the supported POMs and/or supported metal-clusters to obtain recycled supported POMs and/or supported metal-clusters of the present invention, thereafter contacting the recycled supported POMs and/or supported metal-clusters of the present invention with a second organic substrate, which may be the same as or different from the first organic substrate, this process may be repeated many times, preferably at least 4 times, preferably at least 8 times, preferably at least 12 times, preferably at least 100 times.

Due to the definite stoichiometry of POMs, the optionally supported POMs of the present invention can be converted (e.g. by calcination at a temperature exceeding the transformation temperature) to mixed metal-oxide catalysts in a highly reproducible manner. Consequently, the optionally supported POMs according to the present invention can also be used as a precursor for mixed metal-oxide catalysts.

Metal-clusters of the present invention, optionally supported or dispersed in a liquid carrier medium, can be described as nanocatalysts of M", M' and M at the atomic or molecular level, i.e., particles of M", M' and M having an average diameter of about 1.0-2.0 nm, for instance about 1.56 nm, obtained by reduction of the POMs. In the case of all M' being the same as M nanocatalysts with at least one noble atom species are obtained. In the preferred embodiment in which at least one or more or all M' being different from M mixed nanocatalysts with at least one noble atom species and at least one other transition metal species, in most cases another noble metal species, are obtained. In some preferred embodiments nanocatalysts with three different noble metals can be obtained. Thus, the bottom-up approach of the present invention allows for the preparation of noble metal-rich customized nanocatalysts of very well defined size and shape, in which three or more than three metal species can be selected individually from groups that contain or consist of the noble metal elements Rh, Ir, Pd, Pt, Ag, and Au.

The obtained metal-clusters can be used for a wide range of catalytic applications such as in fuel cells, for detection of organic substrates, selective hydrogenation, reforming, hydrocracking, hydrogenolysis and oligomerization. Besides immobilizing the present POMs on a matrix surface and subsequently reducing them, the deposition of the POMs on a surface matrix and their reduction can also be carried out simultaneously.

In addition, e.g., the POMs according to the invention such as a $\{Ag_4[Pd_{13}As_8O_{40}]\}^{10-}$ and $\{Ag_2[Pd_{13}As_8O_{40}]\}^{12-}$ oxo-clusters can be used to produce modified electrodes by electrochemical deposition of the POM on an electrode surface such as a glassy carbon (GC) electrode surface. The obtained deposits contain essentially $M^0$ and $M'^0$ such as $Rh^0$, $Ir^0$, $Pd^0$, $Pt^0$, $Ag^0$, $Au^0$, and preferably mixtures thereof with very small amounts $M\Phi^+$ and $M'\Phi^+$ such as $Pd^{II}$, $Pt^{II}$, $Rh^I$, $Ir^I$, $Ag^I$, $Ag^{III}$, $Au^I$, and $Au^{III}$ and mixtures thereof, preferably $Pd^{II}$, $Pt^{II}$, $Rh^I$, $Ir^I$, $Ag^I$, and $Au^I$. In a preferred embodiment, the obtained deposits provide improved electrochemical behaviors like improved kinetics of electrocatalytic processes compared to a film deposited using a conventional precursor of M and M'. For example, electrodes modified with a deposit of the present POMs can be used for the electrochemical reduction of organic substrates. It has been found that such modified electrodes show a very small overpotential and a remarkably high shelf life.

EXAMPLES

The invention is further illustrated by the following examples.

Example 1: Synthesis of $Na_{10}\{Ag_4[Pd_{13}As_8O_{40}]\}\cdot 36H_2O$ $Pd(CH_3COO)_2$ (0.056 g, 0.23 mmol), $As_2O_5$ (0.020 g, 0.09 mmol), and $AgNO_3$ (0.025 g, 0.15 mmol) were dissolved in 10 mL of 0.5 M sodium acetate solution (pH 7.5). The solution was heated to 80° C. while stirring. During the first 20 min, the pH value of the solution was adjusted to 7.0 by 6 M NaOH. The resulting solution was continually heated at 80° C. for another 80 minutes. Then it was cooled to room temperature, filtered and allowed to crystallize at room temperature in an open vial. Dark brown needle-shaped crystals were obtained after several days, which were collected by filtration and air-dried. Yield: 0.030 g (43% based on Pd). This product was analyzed by XRD, IR, elemental analysis, and bond valence method and was identified as $\{Ag_4[Pd_{13}As_8O_{40}]\}^{10-}$ oxo-cluster ("$Ag_4Pd_{13}$"), isolated as hydrated sodium salt $Na_{10}\{Ag_4[Pd_{13}As_8O_{40}]\}\cdot 36H_2O$ ("Na—$Ag_4Pd_{13}$").

Example 2: Analysis of "Na—$Ag_4Pd_{13}$"

The IR spectrum with 4 cm$^{-1}$ resolution was recorded on a Nicolet Avatar 370 FT-IR spectrophotometer on KBr pellet sample (peak intensities: w=weak; m=medium; s=strong). The characteristic region of the oxo-cluster is between 1000-400 cm$^{-1}$ due to metal-oxygen stretching vibrations: 1634(s), 1384(w), 858(s), 786(s), 656(w), 619(m), 538 (s). The FT-IR spectrum is shown in FIG. 5. Absorption bands that correspond to different vibrational modes of Pd—O groups appear in the regions between 656 and 538 cm$^{-1}$. Absorption bands at 858 cm$^{-1}$ is attributed to the vibrations of $\{AsO_3\}$ groups. The absorption band near 1634 cm$^{-1}$ belongs to asymmetric vibrations of the crystal waters.

Elemental analysis data for "Na—$Ag_4Pd_{13}$", calculated (found): Na 5.85 (5.93), Ag 10.97 (10.56), Pd 35.18 (35.28), As 15.24 (15.52).

Thermogravimetric analysis (TGA) was performed on a SDT Q 600 device from TA Instruments with 10-30 mg samples in 100 μL alumina pans, under a 100 mL/min $N_2$ flow with a heating rate of 5° C./min between 20° C. and 800° C. (FIG. 1). Only one weight-loss step was observed on the thermogram. The weight loss of 17.34 wt % is consistent with a dehydration process up to around 400° C. resulting in a loss of 36 water molecules (calc. 16.49 wt %). This result is in good agreement with that obtained by elemental analysis to determine the amount of water of crystallization present in the POM.

Example 3: Single Crystal X-Ray Diffraction (XRD) Data and Analysis of "Na—$Ag_4Pd_{13}$"

Besides IR, elemental analysis and TGA the product was also characterized by single-crystal XRD. The crystal was mounted in Hampton cryoloop at 173 K using light oil for data collection. Indexing and data collection were carried on a Bruker X8 APEX II CCD single crystal diffractometer with κ geometry and Mo Kα radiation (λ=0.71073 Å). The SHELX software package (Bruker) was used to solve and refine the structure. An empirical absorption correction was applied using the SADABS program as disclosed in G. M. Sheldrick, SADABS, Program for empirical X-ray absorption correction, Bruker-Nonius: Madison, Wis. (1990). The structure was solved by direct method and refined by the full-matrix least squares method ($\Sigma w(|F_o|^2-|F_c|^2)^2$) with anisotropic thermal parameters for all heavy atoms included in the model. The H atoms of the crystal waters were not located. Also, it was not possible to locate all sodium counter cations by XRD, due to crystallographic disorder. The exact number of counter cations and crystal water in the POM were thus based on elemental analysis. Compound "Na—

Ag$_4$Pd$_{13}$" crystallizes in the tetragonal space group P4$_2$/n. Crystallographic data are detailed in Table 1.

TABLE 1

Crystal data for "Na—Ag$_4$Pd$_{13}$"

| | |
|---|---|
| Empirical formula | "Na—Ag$_4$Pd$_{13}$" |
| Formula weight, g/mol | 3932.51 |
| Crystal system | Tetragonal |
| Space group | P4$_2$/n |
| a, Å | 25.8776(9) |
| b, Å | 25.8776(9) |
| c, Å | 12.4329(5) |
| α, ° | 90.00 |
| β, ° | 90.00 |
| γ, ° | 90.00 |
| Volume, Å$^3$ | 8325.7(7) |
| Z | 4 |
| D$_{calc}$, g/cm$^3$ | 3.137 |
| Absorption coefficient, mm$^{-1}$ | 6.974 |
| F(000) | 7360 |
| Theta range for data collection, ° | 1.57-26.45 |
| Completeness to Θ$_{max}$ % | 99.4 |
| Index ranges | -32 <= h <= 32, |
| | -32 <= k <= 32, |
| | -14 <= l <= 15 |
| Reflections collected | 307812 |
| Independent reflections | 8505 |
| R(int) | 0.1012 |
| Absorption correction | Semi-empirical from equilavents |
| Data/restraints/parameters | 8505/0/317 |
| Goodness-of-fit on F$^2$ | 1.085 |
| R$_1$[a], wR$_2$[b] (I > 2σ(I)) | R1 = 0.0567, wR2 = 0.1450 |
| R$_1$[a], wR$_2$[b] (all data) | R1 = 0.0858, wR2 = 0.1751 |
| Largest diff. peak and hole, e/Å$^3$ | 4.265 and -3.662 |

[a]$R_1 = \Sigma\|F_o|-|F_c\|/\Sigma|F_o|$. [b]$wR_2 = [\Sigma w(F_o^2-F_c^2)^2/\Sigma w(F_o^2)^2]^{1/2}$

Example 4: Bond Valence Sum Values for Different Types of Oxygen Atoms in "Na—Ag$_4$Pd$_{13}$"

Bond valence sum values were determined following the method disclosed in I. D. Brown and D. Altermatt, Acta Crystallogr., Sect. B: Struct. Sci., 1985, 41, 244-247. These data are detailed in Table 2.

TABLE 2

Bond valence sum values for different types of oxygen atoms in "Na—Ag$_4$Pd$_{13}$"

| μ$_4$-O (4Pd) | BVS value | μ$_2$-O (Pd—O—As) | BVS value |
|---|---|---|---|
| O1P7 | 1.453 | O2A3 | 1.521 |
| O2P7 | 1.475 | O3A3 | 1.577 |
| O3P7 | 1.490 | O4A3 | 1.548 |
| O4P7 | 1.468 | O1A4 | 1.307 |
| μ$_2$-O (Pd—O—As) | BVS value | O2A4 | 1.532 |
| O1A1 | 1.275 | O3A4 | 1.619 |
| O2A1 | 1.553 | O4A4 | 1.590 |
| O3A1 | 1.548 | Terminal O (Ag) | BVS value |
| O4A1 | 1.612 | O1W | 0.174 |
| O1A2 | 1.289 | O2W | 0.199 |
| O2A2 | 1.539 | O3W | 0.190 |
| O3A2 | 1.570 | O4W | 0.157 |
| O4A2 | 1.578 | O5W | 0.221 |
| O1A3 | 1.317 | O6W | 0.224 |

Example 5: Structure of "Ag$_4$Pd$_{13}$" Oxo-Cluster

The structure of "Ag$_4$Pd$_{13}$" oxo-cluster is displayed in FIGS. 2 and 3. FIG. 4 shows "Ag$_4$Pd$_{13}$" oxo-cluster surrounded by sodium cations. "Ag$_4$Pd$_{13}$" comprises a 13-palladate nanocube [Pd$_{13}$As$_8$O$_{40}$]$^{14-}$ with edge lengths of about 1 nm with the central Pd$^{II}$ ion being coordinated by eight "inner" oxo groups, leading to a slightly distorted {PdO$_8$} core (Pd—O of 2.231(7)-2.428(8) Å). The geometry of the central Pd$^{II}$ ion is cubic and the central Pd$^{II}$ ion is surrounded by twelve Pd$^{II}$ ions all adopting a square-planar geometry comprising a cuboctahedron, which is in turn capped by eight arsenate groups. This assembly is further capped by four Ag$^+$ ions that cover four faces of the Pd13 cage and hence form an equatorial silver belt around the palladium nanocube, with the top and bottom side vacants. Each Ag$^+$ ion is seven-coordinated, including four Ag—Pd heterometallic bonds (2.913(12)-3.044(12) Å) and three terminal water ligands (Ag-Ow=2.395(13)-2.528(8) Å). In the alternative, "Ag$_4$Pd$_{13}$" oxo-cluster can thus also be described as {(Ag(H$_2$O)$_3$)$_4$[Pd$_{13}$O$_{32}$(AsO)$_8$]}$^{10-}$.

Example 6: Synthesis of {Ag$_2$[Pd$_{13}$As$_8$O$_{40}$]}$^{12-}$

Following the synthesis process of example 1, after the crystals of "Na—Ag$_4$Pd$_{13}$" were filtered off, the remaining product was analyzed by XRD and identified as {Ag$_2$[Pd$_{13}$As$_8$O$_{40}$]}$^{12-}$ oxo-cluster ("Ag$_2$Pd$_{13}$"). The product was isolated in the form of its hydrated sodium salt ("Na—Ag$_2$Pd$_{13}$") but the amount of product collected was too small to identify the exact number of sodium counter cations and crystal water.

Example 7: Single Crystal X-Ray Diffraction (XRD) Data and Analysis of "Na—Ag$_2$Pd$_{13}$"

The crystals obtained according to example 6 were analyzed by XRD. The crystal was mounted in Hampton cryoloop at 173 K using light oil for data collection. Indexing and data collection were carried on a Bruker X8 APEX II CCD single crystal diffractometer with κ geometry and Mo Kα radiation (λ=0.71073 Å). The SHELX software package (Bruker) was used to solve and refine the structure. An empirical absorption correction was applied using the SA-DABS program as disclosed in G. M. Sheldrick, SAD-ABS, Program for empirical X-ray absorption correction, Bruker-Nonius: Madison, Wis. (1990). The structure was solved by direct method and refined by the full-matrix least squares method ($\Sigma w(|F_o|^2-|F_c|^2)^2$) with anisotropic thermal parameters for all heavy atoms included in the model. The H atoms of the crystal waters were not located. Also, it was not possible to locate all sodium counter cations by XRD, due to crystallographic disorder. The amount of product collected was too small to perform other types of analysis so the exact number of counter cations and crystal water in the POM could not be determined. Crystal data of "Na—Ag$_2$Pd$_{13}$": triclinic, space group P$_{\bar{1}}$, a=12.4113(7) Å, b=12.5647(7) Å, c=14.2002(8) Å, α=78.263(3)°, β=65.996(2)°, γ=89.905(3)°, V=1972.5(2) Å$^3$, Z=1, R$_1$=0.1030, wR$_2$=0.3055 (I>2σ(I)).

Example 8: Structure of "Ag$_2$Pd$_{13}$" Oxo-Cluster

The structure of "Ag$_2$Pd$_{13}$" is displayed in FIG. 6. As compared to "Ag$_4$Pd$_{13}$" oxo-cluster of examples 1-5, "Ag$_2$Pd$_{13}$" comprises only two Ag$^+$ ions instead of four, these two Ag$^+$ ions being attached to the 13-palladate nanocube [Pd$_{13}$As$_8$O$_{40}$]$^{14-}$ at opposite positions. The geometry of the central Pd$^{II}$ ion is octahedral (coordination number of 6). This indicates that the external, capping Ag$^+$ ions present in "Ag$_4$Pd$_{13}$" lead to a structural readjustment of the palladium-oxo cage, which also involves the orientation of the eight internal oxo-ligands surrounding the central $Pd^{II}$ ion. With an increasing number of capping $Ag^+$ ions, the palladate becomes more rigid with higher symmetry, accompanied by an increasing coordination number of the central $Pd^{II}$ ion.

Example 9: Synthesis of Supported "Na—$Ag_4Pd_{13}$"

Synthesis of Mesoporous Silica support SBA-15

8.0 g of Pluronic® P-123 gel (Sigma-Aldrich) were added to 40 mL of 2M HCl and 208 mL $H_2O$. This mixture was stirred for 2 hours in a water bath at 35° C. until it was completely dissolved. Then 18 ml of tetraethylorthosilicate (TEOS) was added dropwise, and the mixture was kept under stirring for 4 hours. Afterwards, the mixture was heated in an oven at 95° C. for 3 days. The white precipitate was collected by filtration, washed and air-dried. Finally, the product was calcined by heating the as-synthesized material to 550° C. at a rate of 1-2° C. $min^{-1}$ and kept at 550° C. for 6 hours to remove the templates.

Synthesis of Modified SBA-15-apts 1.61 mL of 3-aminopropyltriethoxysilane (apts) was added to 3 g of SBA-15, prepared according to the synthesis described above, in 90 mL toluene. This mixture was refluxed for 5 hours and then filtered at room temperature. The obtained modified SBA-15-apts was heated at 100° C. for 5 hours.

Preparation of "Na—$Ag_4Pd_{13}$" supported on SBA-15-apts (supported "Na—$Ag_4Pd_{13}$")

"Na—$Ag_4Pd_{13}$" was dissolved in water (0.056 mmol/L), resulting in a colored solution. While stirring, SBA-15-apts was slowly added to the solution of "Na—$Ag_4Pd_{13}$" so that the respective amounts of "Na—$Ag_4Pd_{13}$" and SBA-15-apts were 5 and 95 wt %, and the mixture was kept under stirring for 24 hours at 40° C. The mixture was then filtered and washed three times with water. The filtrate was colorless, indicating that the "Na—$Ag_4Pd_{13}$" POM was quantitatively loaded on the SBA-15-apts support, leading to a "Na—$Ag_4Pd_{13}$" POM loading level on the solid support of about 5 wt %. The supported product was then collected and air-dried.

Example 10: Activation of Supported "Na—$Ag_4Pd_{13}$" and Preparation of Supported "$Ag_4Pd_{13}$" Metal Clusters The supported "Na—$Ag_4Pd_{13}$" prepared according to example 9 was activated or transformed into the corresponding supported metal clusters before testing of its catalytic hydrogenation properties.

In a first example 11a, the supported "Na—$Ag_4Pd_{13}$" was activated by air calcination at 550° C. for 4.5 hours. In a second example 11b, the supported "Na—$Ag_4Pd_{13}$" was activated by air calcination at 550° C. for 20 hours. In a third example 11c, the supported "Na—$Ag_4Pd_{13}$" was converted into corresponding supported "$Ag_4Pd_{13}$" metal clusters by a chemical reduction conducted by suspending 100 mg of supported "Na—$Ag_4Pd_{13}$" in 15 mL of water followed by the addition of about 0.25 mL of hydrazine hydrate. The resulting solution was stirred for 1 hour, filtered, dried and then air calcined at 550° C. for 4.5 hours. Without being bound by any theory, it is believed that calcination and optional chemical reduction helps to activate the POM by forming active sites.

Example 12: Catalytic Activity of Supported "Na—$Ag_4Pd_{13}$" and Supported "$Ag_4Pd_{13}$" Metal Clusters The activated supported "Na—$Ag_4Pd_{13}$" of examples 11a and 11b and the supported "$Ag_4Pd_{13}$" metal clusters of example 11c were tested for catalytic hydrogenation of o-xylene.

The hydrogenation of o-xylene was carried out in a 100 mL Parr 5521 stainless steel high-pressure compact reactor equipped with a magnetically coupled stirrer drive ensuring a well-mixed environment of reactants. The reaction mixture contained 3.5 mL of o-xylene in 47.5 mL hexane and 50 mg of activated supported "Na—$Ag_4Pd_{13}$" (5 wt %) and was stirred at 950 rpm. The absence of a diffusion-limited process was confirmed by measuring a similar reaction rate at 1500 rpm. The autoclave was purged with $H_2$ and then heated and pressurized to the desired set point of temperature (300° C. for samples 11a and 11c and 340° C. for sample 11b) and pressure (90 bar for samples 11a and 11c and 128 bar for sample 11b) respectively. In order to ensure catalyst recyclability, adding a new portion of substrate into the reactor after reaction completion followed all catalytic runs (i.e. running more than one cycle).

The reaction was followed by $H_2$ consumption and gas chromatography (GC) analysis. A GC-2010 Shimadzu instrument equipped with a flame ionization detector (FID) was used to measure substrate conversion and selectivity of obtained products via a HP-FFAP column (50 m×0.32 mm) providing good separation of reaction products. The carrier gas was He. This overall procedure ensured good reproducibility of the catalytic experiments.

The SBA-15-apts support alone did not show any hydrogenation activity while supported "Na—$Ag_4Pd_{13}$" and corresponding supported "$Ag_4Pd_{13}$" metal clusters showed catalytic performances with conversion of o-xylene to cis/trans-1,2-dimethylcyclohexane. The conversion and cis/trans selectivity (expressed as cis/trans molar ratio) obtained for the supported "Na—$Ag_4Pd_{13}$" of examples 11a and 11b and for the supported "$Ag_4Pd_{13}$" metal clusters of example 11c are summarized in Table 4 below.

TABLE 4

Catalytic performance

| Sample | Time (h) | Conversion (mol %) | Cis/trans selectivity |
|---|---|---|---|
| 11a | 19 | 14 | 38/62 |
| 11b | 50 | 19 | 38/62 |
| 11c | 22 | 19 | 43/57 |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

Additionally or alternatively, the invention relates to:

Embodiment 1: A polyoxometalate represented by the formula

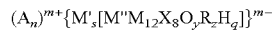

$(A_n)^{m+}\{M'_s[M''M_{12}X_8O_yR_zH_q]\}^{m-}$ or solvates thereof, wherein
each A independently represents a cation,
n is the number of cations,
all M are the same, and are selected from the group consisting of Pd, Pt, Rh, Ir, Ag, and Au, and each M has $d^8$ valence electron configuration,
each M' is independently selected from the group consisting of Rh, Ir, Pd, Pt, Ag, Au, Cd, Hg and mixtures thereof,
s is a number from 1 to 8,
M" is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg and lanthanide metal,
each X is independently selected from the group consisting of Al, Ga, Si, Ge, P, As, Sb, Bi, S, Se, Te and mixtures thereof,
each R is a substituent group which is covalently bonded to X, and each R is independently selected from the group consisting of a hydrogen atom, a substituent group bonded to X via a carbon atom of said substituent group, a substituent group bonded to X via an oxygen atom of said substituent group, a substituent group bonded to X via a sulphur atom of said substituent group, and a substituent group bonded to X via a nitrogen atom of said substituent group,
y is a number from 32 to 40,
z is a number from 0 to 8,
q is a number from 0 to 16, and
m is a number representing the total positive charge m+ of n cations A and the corresponding negative charge m− of the oxo-cluster $\{M'_s[M"M_{12}X_8O_yR_zH_q]\}$.

Embodiment 2: Polyoxometalate of embodiment 1, wherein all M' are the same, and all M' are different from M.

Embodiment 3: Polyoxometalate of embodiment 1 or 2, wherein M is Pd or Pt, M' is Ag or Au, X is P, As, Sb or Bi, and s is 2 or 4, preferably wherein z and q are 0; in particular wherein M is Pd, M' is Ag, X is As, and s is 2 or 4, preferably wherein z and q are 0.

Embodiment 4: Polyoxometalate of embodiment 3, wherein M" is Pd.

Embodiment 5: Polyoxometalate according to any one of the preceding embodiments, wherein
the substituent group R bonded to X via a carbon atom of said substituent group, is selected from the group consisting of
alkyl, cycloalkyl, alkenyl, cycloalkenyl, alkynyl, and aryl; wherein each of said substituent groups may be unsubstituted or substituted;
and each of said substituent groups optionally may contain one or more heteroatoms resulting in hetero-alkyl, hetero-cycloalkyl, hetero-alkenyl, hetero-cycloalkenyl, hetero-alkynyl, and hetero-aryl; and —$CF_3$, —CN, —C(O)O$R^2$, —C(O)$R^2$, and —C(O)N$R^2R^3$;
the substituent group R bonded to X via an oxygen atom of said substituent group, is selected from the group consisting of —O$R^2$, —O(SO$_2$)$R^2$, —O(SO)$R^2$, —O(SO$_2$)O$R^2$, —O(SO)O$R^2$, —OS(O$_2$)N$R^2R^3$, —OS(O)N$R^2R^3$, —OPO(O$R^2$)$_2$, —OPO(O$R^2$)O$R^3$, —OPO($R^2$)O$R^3$, —OC(O)O$R^2$, —OC(O)N$R^2R^3$, and —OC(O)$R^2$;
the substituent group R bonded to X via a sulphur atom of said substituent group, is selected from the group consisting of —SO$_3R^2$, —S$R^2$, —S(O$_2$)$R^2$, —S(O)$R^2$, —S(O)O$R^2$, —S(O)N$R^2R^3$, and —S(O$_2$)N$R^2R^3$; and
the substituent group R bonded to X via a nitrogen atom of said substituent group is selected from the group consisting of —N$R^2R^3$, —N($R^2$)S(O$_2$)$R^3$, —N($R^2$)S(O$_2$)N$R^3R^4$, —N($R^2$)S(O$_2$)O$R^3$, —N($R^2$)S(O)$R^3$, —N($R^2$)S(O)N$R^3R^4$, —N($R^2$)S(O)O$R^3$, —N($R^2$)PO(O$R^3$)$_2$, —N($R^2$)PO(O$R^3$)O$R^4$, —N($R^2$)PO($R^3$)O$R^4$, —N($R^2$)C(O)$R^3$, —N($R^2$)C(O)O$R^3$, —N($R^2$)C(O)N$R^3R^4$ and —NO$_2$;
wherein $R^2$ and $R^3$ are independently selected from the group consisting of H, alkyl, aryl, alkenyl, alkynyl, hetero-alkyl, hetero-cycloalkyl, hetero-alkenyl, hetero-cycloalkenyl, hetero-alkynyl, hetero-aryl and cycloalkyl.

Embodiment 6: Polyoxometalate according to any one of the preceding embodiments, wherein, each A is independently selected from the group consisting of Li, Na, K, Rb, Cs, Mg, Ca, Sr, Ba, Sc, Ti, V, Cr, Mn, Fe, Co, Ni, Cu, Zn, Y, Zr, Ru, Rh, Pd, Pt, Ag, Cd, Lu, Hf, Re, Os, Ir, Pt, Au, Hg, La, lanthanide metal, actinide metal, Sn, Sb, Te, phosphonium, ammonium, guanidinium, tetraalkylammonium, protonated aliphatic amines, protonated aromatic amines or combinations thereof preferably from the group consisting of Li, K, Na and combinations thereof.

Embodiment 7: Polyoxometalate according to any one of the preceding embodiments, represented by the formula

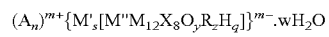

$(A_n)^{m+}\{M'_s[M"M_{12}X_8O_yR_zH_q]\}^{m-} \cdot wH_2O$ wherein w represents the number of attracted water molecules per oxo-cluster $\{M'_s[M"M_{12}X_8O_yR_zH_q]\}$, and ranges from 1 to 100, preferably from 10 to 60, more preferably from 20 to 50.

Embodiment 8: Polyoxometalate according to any one of the preceding embodiments, wherein the polyoxometalate is in the form of particles, preferably wherein at least 90 wt % of the polyoxometalate particles are in the form of primary particles.

Embodiment 9: Process for the preparation of the polyoxometalate according to any one of embodiments 1 to 8, said process comprising:
(a) reacting at least one source of M, at least one source of M' and at least one source of M" with at least one X-containing and optionally R-containing starting material to form a salt of the oxo-cluster $\{M'_s[M"M_{12}X_8O_yR_zH_q]\}$ or a solvate thereof,
(b) optionally adding at least one salt of A to the reaction mixture of step (a) to form a polyoxometalate $(A_n)^{m+}\{M'_s[M"M_{12}X_8O_yR_zH_q]\}^{m-}$ or a solvate thereof, and
(c) recovering the polyoxometalate or solvate thereof.

Embodiment 10: Process according to embodiment 9, wherein in step (a) the concentration of the metal ions originating from the source of M ranges from 0.01 to 1 mole/l, the concentration of the metal ions originating from the sources of M' ranges from 0.001 to 0.1 mole/l, the concentration of the metal ions originating from the source of M" ranges from 0.001 to 0.1 mole/l, and the concentration of the X-containing starting material ranges from 0.001 to 1 mole/l, with the proviso that the ratio of the molar concentration of the metal ions originating from the source of M to the molar concentration of the metal ions originating from the source of M' is in the range from 1 to 20.

Embodiment 11: Process according to embodiments 9, wherein step (a) comprises:
first reacting the at least one source of M and the at least one source of M" with the at least one X-containing and optionally R-containing starting material to form a salt of the polyanion $[M"M_{12}X_8O_yR_zH_q]$ or a solvate thereof,
followed by isolating and optionally purifying said salt of the polyanion $[M"M_{12}X_8O_yR_zH_q]$ or solvate thereof, and reacting said isolated and optionally purified product with at least one source of M' to form the salt of the oxo-cluster {M'$_s$[M"M$_{12}$X$_8$O$_y$R$_z$H$_q$]} or a solvate thereof.

Embodiment 12: Process according to any one of embodiments 9 to 11, wherein water is used as solvent; the at least one source of M is a water-soluble salt of Pt$^{II}$ or Pd$^{II}$, preferably platinum chloride, palladium nitrate, palladium sulphate, palladium chloride or palladium acetate, in particular a salt of Pd$^{II}$ selected from palladium nitrate, palladium sulphate, palladium chloride or palladium acetate; the at least one source of M' is a water-soluble gold or silver salt, preferably selected from gold chloride, gold hydroxide, silver nitrate, silver fluoride or silver chloride, in particular silver nitrate; the at least one source of M" is a water soluble salt of M", preferably selected from palladium acetate, palladium chloride, palladium nitrate and palladium sulfate when M" is palladium; and the at least one source of X is an oxide of X, preferably selected from As$_2$O$_5$, P$_2$O$_5$, Sb$_2$O$_5$, Bi$_2$O$_5$, As$_2$O$_3$, Sb$_2$O$_3$, or Bi$_2$O$_3$, in particular As$_2$O$_5$.

Embodiment 13: Process according to embodiment 12, wherein the at least one source of M" is the same as or different from the at least one source of M, preferably the same.

Embodiment 14: Process according to any one of embodiments 9 to 13, wherein step (a) is carried out in an aqueous solution, and the pH of the aqueous solution ranges from 4 to 10, preferably from 6 to 8, and most preferred from 6.5 to 7.5.

Embodiment 15: Process according to embodiment 14, wherein in step (a) the at least one source of M, the at least one source of M", if applicable the at least one source of M', the at least one source of X containing and optionally the at least one source of R containing starting material are dissolved in a solution of sodium acetate buffer, preferably a 0.1 to 1.0 M solution of sodium acetate buffer, in particular a 0.25 to 0.75 M solution of sodium acetate buffer, and most preferred a 0.50 M solution of sodium acetate buffer.

Embodiment 16: Process according to any one of embodiments 9 to 15, wherein in step (a) the reaction mixture is heated to a temperature of from 20° C. to 100° C., preferably from 70° C. to 80° C.

Embodiment 17: Supported polyoxometalate comprising polyoxometalate according to any one of embodiments 1 to 8 or prepared according to any one of embodiments 9 to 16, on a solid support.

Embodiment 18: Supported polyoxometalate according to embodiment 17, wherein the solid support is selected from polymers, graphite, carbon nanotubes, electrode surfaces, aluminium oxide and aerogels of aluminum oxide and magnesium oxide, titanium oxide, zirconium oxide, cerium oxide, silicon dioxide, silicates, active carbon, mesoporous silica, zeolites, aluminophosphates (ALPOs), silicoaluminophosphates (SAPOs), metal organic frameworks (MOFs), zeolitic imidazolate frameworkds (ZIFs), periodic mesoporous organosilicas (PMOs), and mixtures thereof.

Embodiment 19: Process for the preparation of supported polyoxometalate according to embodiment 17 or 18, comprising the step of contacting polyoxometalate according to any one of embodiments 1 to 8 or prepared according to any one of embodiments 9 to 16, with a solid support.

Embodiment 20: Metal-cluster of the formula

{M'$^o_s$[M"M$^o_{12}$]} wherein
all M$^o$ are the same, and are selected from the group consisting of Pd$^o$, Pt$^o$, Rh$^o$, Ir$^o$, Ag$^o$, and Au$^o$, preferably from Pd$^o$ and Pt$^o$, most preferably Pd$^o$, each M'$^o$ is independently selected from the group consisting of Rh$^o$, Ir$^o$, Pd$^o$, Pt$^o$, Ag$^o$, Au$^o$, Cd$^o$, Hg$^o$ and mixtures thereof, preferably all M'$^o$ are the same and are selected from Ag$^o$ and Au$^o$, most preferably Ag$^o$, s is a number from 1 to 8, preferably 2 to 4, most preferably 2 or 4, in particular 4, and M" is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg and lanthanide metal, and the oxidation state of M" is 0 or greater than 0, preferably M" is Pd, most preferably Pd$^o$.

Embodiment 21: Metal-cluster according to embodiment 20, wherein the metal-cluster is in the form of particles, preferably wherein at least 90 wt % of the metal-cluster particles are in the form of primary particles.

Embodiment 22: Metal-cluster according to embodiment 20 or 21, wherein the metal-cluster is dispersed in a liquid carrier medium thereby forming a dispersion of metal-cluster in said liquid carrier medium; and wherein preferably a dispersing agent is present to prevent agglomeration of the primary particles of metal-cluster, and in particular the dispersing agent forms micelles containing one primary particle of metal-cluster per micelle.

Embodiment 23: Metal-cluster according to embodiment 20 or 21, wherein the metal-cluster is immobilized on a solid support thereby forming supported metal-cluster.

Embodiment 24: Supported metal-cluster according to embodiment 23, wherein the solid support is selected from polymers, graphite, carbon nanotubes, electrode surfaces, aluminium oxide and aerogels of aluminum oxide and magnesium oxide, titanium oxide, zirconium oxide, cerium oxide, silicon dioxide, silicates, active carbon, mesoporous silica, zeolites, aluminophosphates (ALPOs), silicoaluminophosphates (SAPOs), metal organic frameworks (MOFs), zeolitic imidazolate frameworkds (ZIFs), periodic mesoporous organosilicas (PMOs), and mixtures thereof.

Embodiment 25: Process for the preparation of the dispersion of metal-cluster of embodiment 22, said process comprising the steps of
  (a) dissolving the polyoxometalate of any one of embodiments 1 to 8 or prepared according to any one of embodiments 9 to 16, in a liquid carrier medium,
  (b) optionally providing additive means to prevent agglomeration of the metal-cluster to be prepared, and
  (c) subjecting the dissolved polyoxometalate to chemical or electrochemical reducing conditions sufficient to at least partially reduce said polyoxometalate into corresponding metal-cluster.

Embodiment 26: Process for the preparation of the supported metal-clusters of embodiment 23 or 24, comprising the steps of
  (a) contacting the dispersion of metal-cluster of embodiment 22 or prepared according to embodiment 25 with a solid support, thereby immobilizing at least part of the dispersed metal-cluster onto the support and; and
  (b) optionally isolating the supported metal-cluster.

Embodiment 27: Process for the preparation of the supported metal-clusters of embodiment 23 or 24, comprising the steps of
  (a) subjecting the supported polyoxometalate of embodiment 17 or 18 or prepared according to embodiment 19 to chemical or electrochemical reducing conditions sufficient to at least partially reduce said polyoxometalate into corresponding metal-cluster; and
  (b) optionally isolating the supported metal-cluster.

Embodiment 28: Process according to any one of embodiments 25 or 27, wherein the chemical reducing conditions comprise the use of a reducing agent selected from organic and inorganic materials which are oxidizable by $Pd^{II}$, $Pt^{II}$, $Rh^{I}$, $Ir^{I}$, $Ag^{I}$ and $Ag^{III}$, and $Au^{I}$ and $Au^{III}$.

Embodiment 29: Process for the homogeneous or heterogeneous reductive conversion of organic substrate comprising contacting said organic substrate under addition of hydrogen with the polyoxometalate of any one of embodiments 1 to 8 or prepared according to any one of embodiments 9 to 16, and/or with the supported polyoxometalate of embodiment 17 or 18 or prepared according to embodiment 19, and/or with the metal-cluster of embodiment 20 or 21, and/or with the dispersion of metal-cluster of embodiment 22 or prepared according to embodiment 25 or 28, and/or with the supported metal-cluster of embodiment 23 or 24 or prepared according to any one of embodiments 26 to 28.

Embodiment 30: Process according to embodiment 29, comprising:
(a) contacting a first organic substrate under addition of hydrogen with one or more optionally supported polyoxometalates and/or one or more supported metal-clusters,
(b) recovering the one or more optionally supported polyoxometalates and/or the one or more supported metal-clusters;
(c) contacting the one or more optionally supported polyoxometalates and/or the one or more supported metal-clusters with a solvent at a temperature of 50° C. or more, and/or hydrogen stripping the one or more optionally supported POMs and/or one or more supported metal-clusters at elevated temperature, and/or calcining the one or more optionally supported POMs and/or one or more supported metal-clusters at elevated temperature under an oxygen containing gas, e.g. air, or under an inert gas, e.g. nitrogen or argon, to obtain recycled one or more optionally supported polyoxometalates and/or one or more supported metal-clusters;
(d) contacting the recycled one or more optionally supported polyoxometalates and/or the one or more supported metal-clusters under addition of hydrogen with a second organic substrate which may be the same as or different from the first organic substrate; and
optionally repeating steps (b) to (d).

The invention claimed is:

1. A composition comprising a polyoxometalate represented by the formula:

or solvates thereof, wherein:
each A independently represents a cation and is Na,
n is the number of cations and is 10,
all M are the same, and are Pd,
s is 4,
M" is Pd,
each X is As,
y is 40, and
m is 1, and is representing the total positive charge m+ of n cations A and the corresponding negative charge m− of the oxo-cluster $\{M'_s[M''M_{12}X_8O_y]\}$, with M' being Ag.

2. The composition of claim 1, represented by the formula

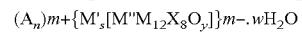

wherein w represents the number of attracted water molecules per oxo-cluster $\{M'_s[M''M_{12}X_8O_y]\}$, and ranges from 1 to 100.

3. The composition of claim 1, wherein said polyoxometalate is in the form of particles,
wherein at least 90 wt % of said polyoxometalate particles are in the form of primary particles.

* * * * *